(12) United States Patent
Dias et al.

(10) Patent No.: US 9,458,256 B2
(45) Date of Patent: Oct. 4, 2016

(54) CARBAMATE, THIOCARBAMATE OR CARBAMIDE COMPRISING A BIOMOLECULAR MOIETY

(75) Inventors: Aylvin Jorge Angelo Athanasius Dias, HE Maastricht (NL); Bartholomeus Johannes Margretha Plum, AJ Ulestraten (NL); Peter Jan Leonard Mario Quaedflieg, KA Elsloo (NL); Roel Wim Wiertz, LC Brunssum (NL)

(73) Assignee: DSM IP ASSETS B.V., Heerlen (NL)

( * ) Notice: Subject to any disclaimer, the term of this patent is extended or adjusted under 35 U.S.C. 154(b) by 1132 days.

(21) Appl. No.: 12/513,576

(22) PCT Filed: Nov. 7, 2007

(86) PCT No.: PCT/EP2007/009637
§ 371 (c)(1),
(2), (4) Date: Nov. 10, 2009

(87) PCT Pub. No.: WO2008/055666
PCT Pub. Date: May 15, 2008

(65) Prior Publication Data
US 2010/0099786 A1     Apr. 22, 2010

(30) Foreign Application Priority Data
Nov. 7, 2006 (EP) .................................... 06023114

(51) Int. Cl.
*C08F 8/30*          (2006.01)
(52) U.S. Cl.
CPC ...................................... *C08F 8/30* (2013.01)
(58) Field of Classification Search
CPC ........................................................ C08F 8/30

USPC ................................................................ 514/1
See application file for complete search history.

(56) References Cited

U.S. PATENT DOCUMENTS

| | | | | |
|---|---|---|---|---|
| 5,932,462 A | * | 8/1999 | Harris et al. .................. | 435/188 |
| 2004/0030101 A1 | * | 2/2004 | Bailon et al. ................. | 530/351 |
| 2004/0038892 A1 | * | 2/2004 | Finn et al. ..................... | 514/12 |
| 2005/0009988 A1 | * | 1/2005 | Harris et al. ................... | 525/56 |
| 2005/0169968 A1 | * | 8/2005 | Elmaleh et al. .............. | 424/426 |

OTHER PUBLICATIONS

Muh et al. Lysineurethanedimethacrylate-a novel generation of amino acid based monomers for bone cements and tissue repair. Biomaterials 23 (2002) 2849-2854.*
International Search Report for PCT/EP2007/009637, mailed Feb. 20, 2008.
Written Opinion of the International Searching Authority for PCT/EP2007/009637, mailed Feb. 20, 2008.
Hern et al., "Incorporation of Adheshion Peptides into Nonadhesive Hydrogels Useful for Tissue Resurfacing", Journal of Biomedical Materials Research, Wiley, New York, NY, US, vol. 39, 1998, pp. 266-276, XP002949005.

\* cited by examiner

*Primary Examiner* — Amina Khan
(74) *Attorney, Agent, or Firm* — Nixon & Vanderhye P.C.

(57) ABSTRACT

Compounds and polymers obtained from such compounds are provided, wherein the compounds have (a) at least two polymerizable moieties, (b) at least one amino acid residue of an amino acid comprising at least two amine groups of which at least two amine groups have formed a carbamate, a thiocarbamate or a carbamide group, and (c) a biomolecular moiety linked directly or via a spacer to the carboxylic acid moiety of the diamino acid residue or a carboxylic acid to which such moiety can be linked.

20 Claims, 15 Drawing Sheets

CARBAMATE, THIOCARBAMATE OR CARBAMIDE COMPRISING A BIOMOLECULAR MOIETY

This application is the U.S. national phase of International Application No. PCT/EP2007/009637, filed 7 Nov. 2007, which designated the U.S. and claims priority to European Application No. 06023114.9, filed 7 Nov. 2006, the entire contents of each of which are hereby incorporated by reference.

FIELD

The invention relates to a polymerisable compound comprising one or more carbamate, thiocarbamate and/or carbamide groups and a biomolecular moiety The invention further relates to a method for preparing such compound, a method for formulating said compound with one or more other compounds, a method of polymerising the compound and an article comprising the compound and a method of preparing such an article.

BACKGROUND AND SUMMARY

The use of synthetic polymers in medical applications, such as in the repair or regeneration of tissues, in particular cartilage, bone or vasculature, has recently attracted significant interest. However, synthetic polymers, for instance polyethylene glycol (PEG) and polyacrylic polymers are generally not capable of selectively facilitating adhesion of cells or facilitate another biospecific function.

Further, several biomolecules, such as peptides, proteins and glycopolymers are readily denatured by heat, proteases, solvents, material processing conditions and/or the manner in which implants are introduced into the body. It is a challenge to provide compositions of synthetic polymers and such biomolecules, whilst retaining the biomolecules in an active form.

There would be great value in attaching biologically active molecules to polymers. Free radical polymerisation is a common method to create protein-polymer hybrid materials as shown in Van Hest et. al. Advances in Polymer Science 2006, 202, 19-52. This free radical polymerisation can also be performed at lower temperatures than condensation polymerisation thereby reducing the risk of denaturing the proteins or biomolecules which are expensive and synthetically intensive to generate. For example, free radical photopolymerisation is often used to prepare hydrogels.

To prepare such protein polymer hybrids by free radical polymerisation the protein or peptide is normally furnished with one polymerisable group as shown by Hubbel et. al. J. Biomed. Mater. Res. 1998, 39, 266. The technique described in this publication may lead to polymers with network defects since the monofunctional peptide functions as a dangling chain end. The consequences are that there is a risk that the peptide is not effectively incorporated into the network and that the resulting polymer be plasticised, to the extent that mechanical properties of the resulting biomaterial are adversely affected. This adverse effect is particularly pronounced with hydrogels.

In *Macromolecules*, Volume 39, Number 4 (2006), page 1305-1307, Junmin Zhu et al. describe the synthesis of a polyethylene glycol diacrylate macromer with a cell-adhesive peptide ligand. The macromer is prepared by reacting a hexapeptide attached to the carboxylic acid of diaminopropionic acid with acryloyl-PEG-anhydrous succinamide (Acr-PEG-NHS), thereby forming amide bonds. In particular, if diamino propionic acid is used in a polymer prone to enzymatic or hydrolytic attack then this non natural amino acid could give rise to an undesired side effect.

In the synthetic approach by Zhu, the polymerisable entities are attached to the peptide to make a crosslinking peptide prepolymer. However the present inventors propose a route where the prepolymer can be furnished with one or more reactive groups that will be able to react with a peptide or activated peptide. This allows better control of peptide density along the polymer chain and furthermore the prepolymer can be polymerised to generate a network that can be subsequently furnished with the biomolecules, in particular peptides. This is in particular advantageous, when the polymer processing conditions are aggressive and the peptides are preferably attached at the end of a process, e.g. in the manufacture of a sensor.

It is an object of the invention to provide a novel polymer or article that may serve as an alternative to known polymers respectively articles, in particular for use in a medical application, a sensor, a diagnostic application and/or a drug delivery application.

It is an object of the invention to provide a polymer or article that shows satisfactory biocompatibility in vivo (such a low tendency or no tendency to cause an immune response) and/or that is biodegradable, in particular in vivo. In particular, it is an object to provide a polymer of which the biodegradation rate under in vivo conditions is well controlled.

It is a further object of the invention to provide a method for efficiently introducing one or more biologically active molecules, such as one or more functional peptides, into a polymer having a polymerisable functionality larger than 1.

It is a further object of the invention to provide a polymer with good degradation behaviour, in particular reduced acidity during degradation.

It is a further object of the invention to provide a novel polymer with good mechanical properties such as a good elasticity.

It is a further object to provide a polymer or article that shows selective interaction with a cell tissue or biological fluid to promote, suppress or balance a specific biological response.

It is a further object of the invention to provide a polymer matrix that is suitable for sensing purposes and/or for targeted drug delivery.

It is a further object to provide a novel compound that can be used to prepare a polymer or article.

It is a further object to provide a novel compound, polymer or article, that can be used in vivo, which comprises a biomolecular moiety that is capable of interacting with (autologous) cells or with a specific biochemical component, or that comprises a functional group that can be covalently attach with such biomolecular moiety.

It is a further object of the invention to provide an article comprising a coating based on the polymer which can be used to coat implanted articles One or more other objects that may be solved in accordance with the present invention will become apparent from the description, below.

It has been found possible to meet one or more objects of the present invention by providing a compound comprising (a) at least two polymerisable moieties, (b) at least one amino acid residue of an amino acid comprising at least two amine groups of which at least two amine groups have formed a carbamate, a thiocarbamate or a carbamide group, and (c) a biomolecular moiety linked directly or via a spacer to the carboxylic acid moiety of the diamino acid residue.

In particular the invention relates to a compound, which is polymerisable, represented by formula I

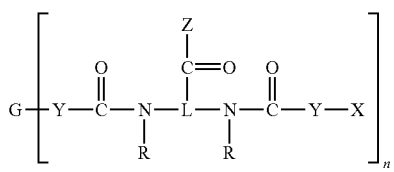

Formula I wherein
G is a residue of a polyfunctional compound having at least n functional groups or a moiety X
each X independently represents a moiety comprising a polymerisable group;
each Y independently represents, O, S or NR;
each R independently represents hydrogen or a group selected from substituted and unsubstituted hydrocarbons which optionally contain one or more heteroatoms, preferably hydrogen or a C1-C20 hydrocarbon, more preferably hydrogen or a C1-C8 alkyl;
L represents a substituted or unsubstituted hydrocarbon which optionally contains one or more heteroatoms.
n is an integer having a value of 1 in case G represents an X and n is at least 2, preferably 2-8, in case G represents a residue of a polyfunctional compound having at least n functional groups;
Z is a biomolecular moiety linked directly or via a spacer to the remainder of the compound.

DETAILED DESCRIPTION

Figure 1:
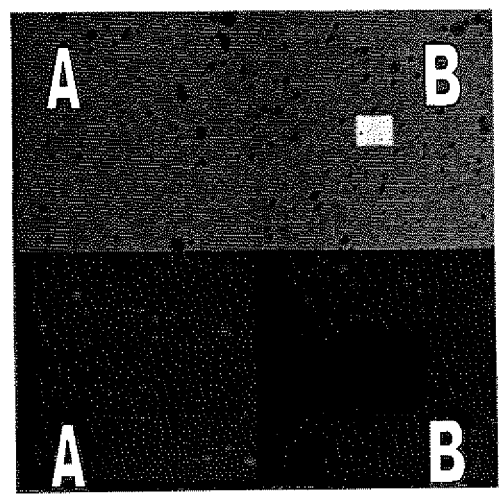
FIG. 1 shows photographic patterning of $PEG_{600}$(LDI-HEA)$_2$ with UV masking group for gel 32 according to Example 2.

Within the context of the present invention the term "hydrocarbon" is meant to include substituted and unsubstituted hydrocarbons, hydrocarbons with one or more heteroatoms (such as S, N, O, P) or hydrocarbons without heteroatoms, unless specifically mentioned otherwise. Substituents may in particular be selected from —OH and halogen atoms (Br, Cl, F, I).
The term "alkyl" and "alkylene" is meant to include unsubstituted and substituted alkyl respectively alkylene, unless specified otherwise. Substituents may in particular be selected from —OH and halogen atoms (Br, Cl, F, I).

In principle, the polymerisable moiety ("X") in the polymerisable compound according to the present invention can be any moiety that allows the formation of a polymer. In particular it may be chosen from moieties that are polymerisable by an addition or radical reaction. The addition reaction has been found easy and well-controllable. Further, it may be carried out without formation of undesired side products, such as products formed from leaving groups.
Preferably, the moiety allows radical polymerisation. This has been found advantageous as it allows initiating a polymerisation, in the presence of a photo-initiator, by electromagnetic radiation, such as UV, visible, microwave, Near IR, gamma radiation, or by electron beam instead of thermally initiating the polymerisation reaction. This allows rapid polymerisation, with no or at least a reduced risk of thermal denaturation or degradation of (parts of) the compound/the polymer.
Thermal polymerisation may be employed, in particular in case no biological moiety or moieties are present that would be affected by heat. E.g. heat-polymerisation may be employed when one or more short chain peptides and/or proteins are present of which the bio-active sites are not affected by the high temperature, required for polymerization.
Preferred examples of polymerisable groups X include groups comprising an unsaturated carbon carbon bond—such as a C=C bond (in particular a vinyl group) or a C≡C group (in particular an acetylene group), thiol groups, epoxides, oxetanes, hydroxyl groups, ethers, thioethers, HS—, $H_2N$—, —COOH, HS—(C=O)— or a combination thereof, in particular a combination of thiol and C=C groups.
In particular preferred is a polymerisable moiety X selected from the group consisting of acrylates methacrylates, alkyl(meth)acrylates, hydroxyl alkyl(meth)acrylates; vinylethers; alkylethers; itaconates, unsaturated diesters and unsaturated diacids or salts thereof (such as fumarates); vinylsulphones, vinylphosphates, alkenes, unsaturated esters, fumarates, maleates and combinations thereof. Such moieties X can be introduced in the polymer of the present invention starting from readily available starting materials and show good biocompatibility, which makes them particularly useful for an in vivo or other medical application.
Good results have in particular been achieved with moieties X being hydroxyethylacrylate and hydroxyethylmethacrylate
In an advantageous embodiment, the polymerisable moiety X is represented by the formula —$R_1R_2C=CH_2$, wherein
$R_1$ is chosen from the group consisting of substituted and unsubstituted, aliphatic, cycloaliphatic and aromatic hydrocarbon groups that optionally contain one or more moieties selected from the group consisting of ester moieties, ether moieties, thioester moieties, thioether moieties, carbamate moieties, thiocarbamate moieties, amide moieties and other moieties comprising one or more heteroatoms, in particular one or more heteroatoms selected from S, O, P and N. $R_1$ may be linear or branched. In particular $R_1$ may comprise 2-20 carbon atoms, more in particular it may be a substituted or unsubstituted $C_1$ to $C_{20}$ alkylene; more in particular a substituted or unsubstituted $C_2$ to $C_{14}$ alkylene; and
$R_2$ is chosen from the group consisting of hydrogen and substituted and unsubstituted alkyl groups, which alkyl groups optionally contain one or more heteroatoms, in particular one or more heteroatoms selected from P, S, O and N. $R_2$ may be linear or branched. In particular, $R_2$ may be hydrogen or a substituted or unsubstituted $C_1$ to $C_6$ alkyl, in particular a substituted or unsubstituted $C_1$ to $C_3$ alkyl.

The amino acid residue ("L") is a substituted or unsubstituted hydrocarbon, which may contain heteroatoms, such as N, S, P and/or O. In case of a substituted hydrocarbon the substituent may be a hydroxyl.

The amino acid residue may be based on a D-isomer or an L-isomer. Preferably, L is C1-C20 hydrocarbon, more preferably, L is a linear or branched C1-C20 alkylene, even more preferably C1-C12 alkylene, most preferably C3-C8 alkylene, wherein the alkylene may be unsubstituted or substituted, in particular with a hydroxyl, and/or optionally contains one or more heteroatoms. In view of desirable hydrophilic properties, the amount of carbons is preferably relatively low, such as 8 or less.

Particularly preferred are amino acid residues selected from lysine, ornithine, hydroxyllysine, N-alpha-methyl lysine or diaminobutanoic acid residues.

In particular in case the compound/polymer/article of the present invention is intended to be used in a medical application, more in particular in case it is intended to be used in vivo, it is preferred that the amino acid residue is based upon a naturally amino acid, usually an L-isomer. This is in particular desired in case the compound/polymer/article is biodegradable. In view thereof, preferred amino acid residues are residues of L-lysine, L-hydroxylysine or N-alpha-methyl-lysine. Good results have in particular been achieved with L-lysine.

In case the compound/polymer of the invention degrades (for instance in vivo), an amino acid (corresponding to the residue "L") may be one of the degradation products. As the compound/polymer degrades, acid (protons, $H_3O^+$) may be released. This may cause an inflammation or similar reaction, under in vivo conditions. The inventors consider that the amino acid may contribute to avoiding an inflammation of tissue in the vicinity of a biodegrading implanted article of the invention. Without being bound by theory, it is contemplated that the amino acid may scavenge the acid, thereby contributing to avoiding an inflammation of the tissue. For this purpose lysine is found particularly suitable.

L-Hydroxylysine may be useful in that it allows the attachment of a peptide via the C terminus of the peptide to be attached. It may also be used for providing a polymer with a higher hydrophilicity than a comparable polymer based on L-lysine.

The amino acid which may be formed upon degradation of a compound/polymer of the invention may serve a physiological function, such as contribute to the healing of a wound (L-arginine, L-glutamine) or affect the nervous system (L-asparagine), e.g. in case of a nerve guide comprising the polymer.

As indicated above, Z is a biomolecular moiety linked directly or via a spacer to the remainder of the compound. The spacer may be present to provide selective surface or bulk patterning of the biomolecular moiety. The biomolecular moiety Z can in principle be any biologically active molecule bound (directly or via a spacer) to the carboxylic acid group of the amino acid residue. Such molecule can be a naturally occurring molecule or a synthetic molecule.

Preferably, the biomolecular moiety Z is selected from cell signalling moieties, moieties capable of improving cell adhesion to the compound/polymer/article, moieties capable of controlling cell growth (such as stimulation or suppression of proliferation), antithrombotic moieties, moieties capable of improving wound healing, moieties capable of influencing the nervous system, moieties having selective affinity for specific tissue or cell types, epitopes and antimicrobial moieties. The moiety may exert an activity when bound to the remainder of the compound/polymer/article and/or upon release from the compound. Preferably, it is active when bound.

Preferably, the biomolecular moiety Z is selected from amino acids, peptides, including cyclic peptides, oligopeptides, polypeptides, glycopeptides and proteins, including glycoproteins; nucleotides, including mononucleotides, oligonucleotides and polynucleotides and carbohydrates.

For instance, an amino acid may be linked for stimulating wound healing (L-arginine, L-glutamine) or to modulate the functioning of the nervous system (L-asparagine).

In a preferred embodiment, the bioactive moiety is a peptide residue, more preferably an oligopeptide residue. Peptides with specific functions are known in the art and may be chosen based upon a known function. For instance, the peptide may be selected from growth factors and other hormonally active peptides. In particular, Z may be selected from a peptide residue comprising the sequences as given below, which are composed of amino acids known by a man skilled in the art.

| Peptide residue | suggested function |
|---|---|
| RGD, GRGDS, RGDS | Enhance bone and/or cartilage tissue formation; Regulate neurite outgrowth; Promote myoblast adhesion, proliferation and/or differentiation; Enhance endothelial cell adhesion and/or proliferation |
| KQAGDV | Smooth muscle cell adhesion |
| YIGSR | Cell adhesion |
| REDV | Endothelial cell adhesion |
| GTPGPQGIAGQRGVV (P-15) | Cell adhesion (osteoblasts) |
| PDGEA | Cell adhesion (osteoblasts) |
| IKVAV | Neurite extension |
| RNIAEIIKDI | Neurite extension |
| KHIFSDDSSE | Astrocyte adhesion |
| VPGIG | Enhance elastic modulus of artificial extra cellular matrix (ECM) |
| FHRRIKA | Improve osteoblastic mineralization |
| KRSR | Osteoblast adhesion |
| KFAKLAARLYRKA | Enhance neurite extension |
| KHKGRDVILKKDVR | Enhance neurite extension |
| YKKIIKKL | Enhance neurite extension |
| NSPVNSKIPKACCVPTELSAI | Osteoinduction |
| APGL | Collagenase mediated degradation |
| VRN | Plasmin mediated degradation |
| AAAAAAAA | Elastase mediated degradation |

-continued

| Peptide residue | suggested function |
|---|---|
| Acetyl-GCRDGPQ-GIWGQDRCG | Encourage cell-mediated proteolytic degradation, remodeling and/or bone regeneration (with RGD and BMP presentation in vivo) |

In an embodiment, Z is angiotensin. Angiotensin may be used to impart vasoconstriction, increased blood pressure, and/or release of aldosterone from the adrenal cortex.

A preferred example of a cyclic peptide is gramicidin S, which is an antimicrobial.

Further examples of suitable peptides in particular include: vascular endothelial growth factor (VEGF), transforming growth factor B (TGF-B), basic fibroblast growth factor (bFGF), epidermal growth factor (EGF), osteogenic protein (OP), monocyte chemoattractant protein (MCP 1), tumour necrosis factor (TNF).

Examples of proteins which may in particular form part of the compound of the present invention include growth factors, chemokines, cytokines, extracellular matrix proteins, glycosaminoglycans, angiopoetins, ephrins and antibodies.

A preferred carbohydrate is heparin, which is antithrombotic.

A nucleotide may in particular selected from therapeutic oligo-nucleotides, such as a oligo-nucleotide for gene therapy and oligo-nucleotide that are capable of binding to cellular or viral proteins, preferably with a high selectivity and/or affinitity.

Preferred oligo-nucleotides include aptamers. Examples of both DNA and RNA based aptamers are mentioned in Nimjee at. Al. Annu. Rev. Med. 2005, 56, 555-583. The RNA ligand TAR (Trans activation response), which binds to viral TAT proteins or cellular protein cyclin T1 to inhibit HIV replication, is an example of an aptamer. Further, preferred nucleotides include VA-RNA and transcription factor E2F, which regulates cellular proliferation.

As indicated above, the biomolecular moiety may be linked via spacer. In principle any spacer may be used that can be coupled with both the carboxylic acid of the amino acid residue of the compound/polymer of the invention and the biomolecule to be covalently attached. Suitable spacers include polyalkylene glycols, such as PEG, oligomeric esters or peptide segments that have no signalling functions e.g. oligopeptides or polypeptides based on one amino acid, such as glycine.

The moiety G which may be present in the compound/polymer of the present invention may be the residue of any molecule comprising at least n functionalities that can be linked with the moiety L via a —Y—(C═O)—NR— bond. In particular such residue may be selected from the group consisting of multifunctional polymers and oligomers comprising one or more of the following functionalities: —OH, —NH$_2$, —RNH, —SH, wherein R is as defined above.

In particular, the polyfunctional molecule respectively G may be selected from poly(lactic acid) (PLA); polyglycolide (PGA); poly(anhydrides); poly(trimethylenecarbonates); poly(orthoesters); poly(dioxanones); poly(ε-caprolactones) (PCL); poly(urethanes); poly(vinyl alcohols) (PVA); poly alkylene glycols, preferably PEG; polyalkylene oxides, preferably selected from poly(ethylene oxides) and poly(propylene oxides); poloxamers; meroxapols; poloxamines; poly (hydroxy acids); polycarbonates; polyaminocarbonates; poly(vinyl pyrrolidones); poly(ethyl oxazolines); carboxymethyl celluloses; hydroxyalkylated celluloses, such as hydroxyethyl cellulose and methylhydroxypropyl cellulose; and natural polymers, such as polypeptides, polysaccharides and carbohydrates, such as polysucrose, hyaluronic acid, dextran and similar derivatives thereof, heparan sulfate, chondroitin sulfate, heparin, alginate, and proteins such as gelatin, collagen, albumin, or ovalbumin; and co-oligomers, copolymers, and blends of any of these moieties.

The moiety G may be chosen based upon its biostability/biodegradability properties. For providing a compound/polymer/article with a high biostability, polyethers, polythioethers, aromatic polyesters, aromatic thioesters are generally particularly suitable. Preferred examples of oligomers and polymers that impart biodegradability include aliphatic polyesters, aliphatic polythioesters, aliphatic polyamides and aliphatic polypeptides.

Preferably G is selected from polyesters, polythioesters, polyorthoesters, polyamides, polythioethers, polyethers, polyanhydride or polydioxanone. Good results have in particular been achieved with a polyalkylene glycol, more in particular with a PEG.

For a hydrophobic polymer, G may suitably be selected from hydrophobic polyethers such as polybutylene oxide or poly(-methyl-1,4-butanediol)co(tetramethyleneglycol) (PTGL).

A polyalkylene glycol, such as PEG is advantageous in an application wherein the compound or polymer of the present invention may be in contact with a protein containing body fluid for instance blood, plasma, serum or the extracellular matrix. It may in particular show a low tendency to foul (low non-specific protein absorption) and/or have an advantageous effect on the adhesion of biological tissue. A low fouling is desirable, in order to avoid shielding of group Z by fouling proteins and the like.

The number average molecular weight (Mn) of the moiety G is usually at least 200 g/mol, in particular at least 500 g/mol. For an improved mechanical property, Mn preferably is at least 2000 g/mol. The number average molecular weight of the moiety G is usually up to 100 000 g/mol. The number average molecular weight is as determinable by size exclusion chromatography (GPC).

The invention further relates to a method for preparing the compound according to the present invention comprising first reacting a compound with formula III

Formula III wherein R is hydrogen or a protecting group with a compound of the formula X—Y—H and—if G is different from X—a compound of the formula G-Y—H wherein the hydrogen or protecting group is selectively removed to covalently attach the biomolecular moiety directly or via a spacer to the carboxylic acid moiety attached to L.

It is an advantage of the method of the invention that it can be carried out without the formation of undesired by-products (molecules formed from as leaving groups).

Suitable and preferred reaction conditions may be based on conditions known in the art for reacting an isocyanate with an amine, alcohol or thiol. If desired, the protective group may be removed in a manner known in the art. For instance it may be removed by exposure to light in case of a photocleavable group. An alkyl may chemically be removed (for instance methyl), by exposure to a base (for instance methyl) or by acidic hydrolysis, e.g. in trifluoro acetic acid (for instance t-butyl).

The present invention also relates to a polymer comprising the polymerisable compound and to an article, in particular an article for medical use, comprising the polymerisable compound.

The present invention also relates to a polymer comprising a certain proportion of the polymerisable compounds and a radically or addition polymerisable compound such that an optimal biologic effect is observed. The radically or addition polymerisable compound may be chosen from the above described polymerisable moieties X.

The polymers according to the present invention preferably further comprise compounds of formula II

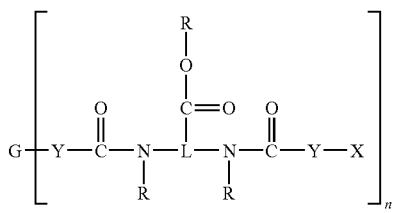

wherein R is selected from hydrogen, substituted or unsubstituted alkyl, substituted or unsubstituted aryl or a metal salt.

As used herein, the term "polymer" denotes a structure that essentially comprises a multiple repetition of units derived, actually or conceptually, from molecules of low relative molecular mass. Such polymers may include homopolymers, copolymers, block copolymers, crosslinked networks, branched polymers and linear polymers. Oligomers are considered a species of polymers, i.e. polymers having a relatively low number of repetitions of units derived, actually or conceptually, from molecules of low relative molecular mass.

As used herein, the term "prepolymer" denotes a polymer comprising one or more polymerisable functionalities, for instance vinyl groups.

Polymers may have a molecular weight of 200 Da or more, 400 Da or more, 800 Da or more, 1000 Da or more, 2000 Da or more, 4000 Da or more, 8000 Da or more, 10 000 Da or more, 100 000 Da or more or 1 000 000 Da or more. Polymers having a relatively low mass, e.g. of 8000 Da or less, in particular 4000 Da or less, more in particular 1000 Da or less may be referred to as oligomers.

It has in particular been found that the polymer or the article of the present invention show one or more of the following properties: being hypo- or non-allergenic, having a high biocompatibility, having a good elasticity, elongation until rupture and/or high toughness, showing a low tendency to fouling, showing favorable cell adhesion, being capable of allowing cell colonisation, being biodegradable or biostable, showing reduced acidity upon degradation, more effective tying in of biologically active moieties and low cytotoxicity.

More in particular, it has been found possible to provide a polymer that shows low or no fouling by non specific protein absorption, e.g., when contacted with a body fluid that contains a protein and/or that allows adhesion of cells and/or colonisation by cells, in vivo and/or in vitro.

It is further contemplated that the polymer according to the present invention may protect a biomolecular moiety, at least to some extent to a detrimental effect, such as loss of activity, as a result of denaturation by heat, proteases, solvents, material processing conditions and/or the manner the polymer may be introduced into the body (e.g. as an implant).

The article of the present invention may be tubes, microspheres, nanospheres, porous monolith wax, woven or non-woven fibrous material, filaments, films, foams, implants, gels, hydrogels, sponges, coatings and artificial body tissues.

The polymerisable compound or polymer according to the invention may in particular be used to provide a medical device, more in particular a prosthesis or another substitute for a tissue, a drug delivery device, microspheres, an implantable device or an extracorporeal medical device. The polymer is in particular suitable to prepare a biostable or biodegradable polymer device for engineering of tubular tissues. These tissues include intestine, blood vessels, tracheas, ureters and nerve guides.

The polymers according to the present invention may also be used to prepare coatings, films, sealants and adhesives for medical applications. The polymer may also be given a 3 D shape by a 3D modelling (also known as rapid manufacturing) process, such as a layer by layer manufacturing process.

The invention further relates to a method for the preparation of the polymer according to the present invention by polymerizing the compounds of formula I.

The invention further relates to a method for preparing the polymer by polymerizing a compound of formula II,

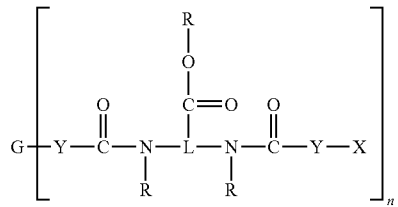

wherein R is selected from hydrogen or a protecting group wherein hydrogen or the protecting group is selectively removed and subsequently the biomolecular moiety is covalently attached directly or via a spacer to the carboxylic acid moiety attached to L.

The biomolecular moiety may be covalently attached to the carboxylic acid in a manner known in the art, in particular using an amidation or esterification reaction.

The polymer of the invention may be obtained by polymerising the polymerisable moieties of a compound according to the invention. This may be done based upon a method known in the art for the particular polymerisable moiety, e.g. step growth polymerisation or radical polymerisation. The polymerisation may be initiated using a low temperature thermal initiator or a photo-initiator. Preferably the polymerisation is initiated using a photo-initiator.

A single photo initiator or two or more photo initiators can be included. In order to increase curing speeds a combination of photo initiators may be advantageously used, especially if colorants are present.

Suitable photo initiators are well known and within the skill of the art, and include free-radical photo initiators. Free-radical photo initiators are generally divided into two classes according to the process by which the initiating radicals are formed.

Compounds that undergo uni-molecular bond cleavage upon irradiation are termed Type I photo initiators. If the excited state photo initiator interacts with a second molecule (a coinitiator COI) to generate radicals in a bimolecular reaction, the initiating system is termed a Type II photo initiator. Examples of suitable alpha-cleavage homolytic free-radical photo initiators (Type I) are benzoin derivatives, methylolbenzoin and 4-benzoyl-1,3-dioxolane derivatives, benzilketals, α,α-dialkoxyacetophenones, α-hydroxy alkylphenones, α-aminoalkylphenones, acylphosphine oxides (under which also bisacylphosphine oxides), acylphosphine sulphides, halogenated acetophenone derivatives, and the like.

Further examples of the photo-polymerization initiator are 1-hydroxycyclohexylphenyl ketone, 2,2-dimethoxy-2-phenylacetophenone, xanthone, fluorenone, benzaldehyde, fluorene, anthraquinone, triphenylamine, carbazole, 3-methylacetophenone, 4-chlorobenzophenone, 4,4'-dimethoxybenzophenone, 4,4'-diaminobenzophenone, Michler's ketone, benzoin propyl ether, benzoin ethyl ether, benzyl methyl ketal, 1-(4-isopropylphenyl)-2-hydroxy-2-methylpropan-1-one, 2-hydroxy-2-methyl-1-phenylpropan-1-one, thioxanethone, diethylthioxanthone, 2-isopropylthioxanthone, 2-chlorothioxanthone, 2-methyl-1-[4-(methylthio) phenyl]-2-morpholino-propan-1-one, 2,4,6-trimethylbenzoyldiphenylphosphine oxide, bis-(2,6-dimethoxybenzoyl)-2,4,4-trimethylpentylphosphine oxide, bis-(2,4,6-trimethylbenzoyl)-phenylphosphine oxide, camphorquinon, eosine and the like. Mixtures of these photo-polymerization initiators may also be used.

Examples of commercially available products of the photo-polymerization initiator include IRGACURE 184, 369, 651, 500, 907, CGI1700, 1750, 1850, 819, 2959, CG24-61, Darocur I116, 1173 (manufactured by Ciba Specialty Chemicals Co., Ltd.), Lucirin LR8728 (manufactured by BASF), Ubecryl P36 (manufactured by UCB), and the like.

Further examples of Type II photo initiator are triethylamine, diethylamine, N-methyldiethanoleamine, ethanolamine, 4-dimethylaminobenzoic acid, methyl 4-dimethylaminobenzoate, ethyl 4-dimethylaminobenzoate, isoamyl 4-dimethylaminobenzoate, and the like. As commercially available products of the photosensitizer, for example, Ebecryl P102, 103, 104, and 105 (manufactured by UCB) are given. Use of mixtures is also possible.

In case the polymer is to be provided with a biomolecular moiety, such moiety may be covalently attached to the polymer after the polymerisation.

As indicated above, the invention also relates to an article comprising a polymer according to the invention. The article or a considerable part thereof may be made of a polymer of the invention or a composition comprising such polymer, for instance in addition to a bioactive agent, in particular a pharmaceutical that may be released from the article.

Preferably at least part of a surface of the article comprises the polymer.

If desired, the article can be provided with different moieties Z at different parts of the article, for instance at different parts of the surface. Thus different desired effects may occur at different parts of the article (e.g. in vivo). For instance, this may allow to control a growth direction for specific cells, such as nerve cells in case the article is a nerve guide. If desired, a part of the article may be provided with a biomolecular moiety and another part with a protective group, thereby stimulating a specific effect only at a targeted part of the article.

In particular this may be desired at the surface of the article. Accordingly, in a preferred embodiment at least a first selected area of the surface of the article comprises a first polymer or a first part of a polymer containing a biomolecular moiety as moiety Z or as a part of moiety Z and wherein at least a second area comprises a second polymer of the invention or a second part of the same polymer containing a moiety different from said biomolecular moiety, e.g. a hydrogen, a protecting group or a different biomolecular moiety.

Such an article may in particular be prepared by
shaping the article using a compound or polymer according to the invention, wherein R is a protecting group (preferably a photocleavable group) or wherein R is hydrogen,
selectively removing the protecting (photocleavable) group at the area at which the biomolecule is to be bound and attachment of the biomolecular moiety directly or via a spacer to the carboxylic acid moiety.

R may in particular be hydrogen or a protective group in case a biomolecular moiety is not desired for the intended purpose or in case the compound/polymer/article is still to be subjected to a treatment, such as a treatment which may be detrimental to the biomolecular moiety. In the latter case the biomolecular moiety may be bound to the compound/polymer/article after such treatment, if desired. In particular, a protective group may be used to protect the carboxylic acid from reacting with other reactive moieties in the compound/polymer itself or with another molecule. A protective group may also be used to allow or facilitate binding a biomolecular moiety in a specific pattern. Suitable protective groups include alkyls, in particular unsubstituted alkyls such as methyl, ethyl and C3-C8 unsubstituted alkyls. Methyl and C3-C8 alkyls, in particular t-butyl, are preferred alkyls.

In case R is a protective group is may advantageously be selected from photocleavable groups, as these as easily removable, by using electromagnetic radiation, It is also possible to remove such groups easily in a specific pattern, e.g. on a surface of an article of the invention, by selective irradiation of specific parts of the surface. Preferred examples of photocleavable groups include those cited in Protective groups in Organic synthesis, Theodora Greene, 3$^{rd}$ Edn Wiley ISBN 0 471-16019 (1999).

It is also possible to select a protective group that is removable by acid treatment, e.g. by contacting with a trifluoroacetic acid solution. An example of a protective group removable by acid is t-butyl.

Preferably, the protecting group is a photocleavable group.

Preferably the selective removing is accomplished by selectively irradiating the surface of the polymer with electromagnetic radiation.

The invention will now be illustrated by the following examples without being limited thereto.

EXAMPLES

Materials dl-Lactide and glycolide were purchased from PURAC. L-lysine-diisocyanate tert-butylester was purchased from Symochem (Eindhoven, The Netherlands). L-lysine-diisocyanate methyl ester was provided by Kyowa Hakko Europe GmbH. Caprolactone was provided by Solvaycaprolactone. Arg(Pmc)-Gly-Asp(O$^t$Bu)-O$^t$Bu and Gly-Arg(Pmc)-Gly-Asp(O$^t$Bu)-Ser-(O$^t$Bu)$_2$ were purchased from Chiralix (Nijmegen, The Netherlands). Pmc and $^t$Bu stand for the protective groups 2,2,5,7,8-pentamethylchroman-6-sulfonyl and tertiary butyl, respectively. All other chemicals were purchased from Aldrich. The chemicals were used as such unless otherwise stated.

Instrumentation

NMR Advance 300 MHz spectrometer (Bruker), Agilent 1100 MSD single quat LCMS, Perkin Elmer Spectrum and FTIR spectrometer were used to characterize the chemical structure and purity. Silica gel column chromatography (SGCC) was performed using Acros silica gel (0.035-0.070 mm, pore diameter ca. 6 nm).

TLC was carried out on Merck precoated silica gel 60 F-254 plates. Compounds were visualized by UV or ninhydrin.

A Laminar flow cabinet (Clean Air DLF/RS6), a incubator (NAPCO model 6300), a Olympus CK2 microscope, equipped with a monochrome CCD camera (ADIMEX Image Systems, MX5) connected to a computer with Optimas image analysis software (BioScan Optimas) were used.

Example 1

Preparation of Materials

Synthesis of p-(lactide-co-glycolide)1000 diol (1)

dl-Lactide (24.76 g, 17.2 mmol), glycolide (19.94 g, 17.2 mmol) and diethyleneglycol (5.306 g, 50 mmol) were melted at 150° C. tin(II)-ethylhexanoate (13.9 mg) was added as a catalyst. The reaction was allowed to proceed for 18 h upon which the reaction mixture was cooled to room temperature to obtain 1.
$^1$H-NMR (300 MHz, CDCl$_3$, 22° C., TMS): δ (ppm)= 5.25-5.18 (m, 5.3H, CH(lac)); 4.83-4.74 (m, 10.6H, CH$_2$ (gly)); 4.30 (m, 6.7H, —(C=O)OCH$_2$CH$_2$O—, —O(C=O) CH$_2$OH, —O(C=O)CH(CH$_3$)OH); 3.70 (m, 4H, —(C=O) OCH$_2$CH$_2$O—); 2.79 (broad, 2H, —OH); 1.58 (m, 19.1H, CH$_3$(lac))

Synthesis of p-(lactide-co-Glycolide)1000-(t-Bu-LDI-HEA)$_2$ (2)

Hydroxyethylacrylate (HEA, 1.16 g, 10 mmol) was added dropwise to a solution of L-lysine-diisocyanate tert-butylester (2.54 g, 10 mmol), Tin-(II)-ethylhexanoate (0.012 g, 0.028 mmol), Irganox 1035 (0.012 g) in THF (17.4 gram) and dry air at controlled temperature (<20° C.). The reaction was monitored with GPC w.r.t to the presence of HEA. After 18 hours 1 (5 gram, 5 mmol) was added at room temperature. The temperature was gradually increased till 60° C. until the IR vibrational stretch of NCO group at v=2260 cm$^{-1}$ disappeared. When the reaction was complete, based on IR spectroscopy the solvent was evaporated. 2 was obtained without further purification as a slightly coloured yellow oil.
$^1$H-NMR (300 MHz, CDCl$_3$, 22° C., TMS): δ (ppm)=6.5- 6.0 (6H, CH, acrylate), 5.5 (2H, NHCO), 5.3 (2H, NHCO); 5.25-5.18 (m, H, CH(lac)); 4.83-4.74 (m, 2H, CH$_2$(gly)); 4.30 (m, 6.7H, —(C=O)OCH$_2$CH$_2$O—, —O(C=O) CH$_2$OH, —O(C=O)CH(CH$_3$)OH); 4.3-4.1 (m, CH$_2$, CH (Lys), and CH$_2$, HEA); 3.70 (m, 4H, —(C=O) OCH$_2$CH$_2$O—); 3.1 (m, 4H, Lys); 1.8-1.3 (8H, Lys, 12H, t-Butylester, m, 4H, CH$_2$ (Lys)) 1.58 (m, 19.1H, CH$_3$(lac))

Synthesis of p-(Lactide-co-Glycolide)1000 diacrylate (3)

1 (50 gram, 50 mmol) and triethyleneamine (10.63 g, 0.105 mol) was dissolved in 100 mL tetrahydrofuran (THF). Acryloylchloride (9.5 g, 0.105 mol) dissolved in THF (15 mL) was added dropwise to the solution at controlled temperature (<5° C.). The reaction mixture was stirred at room temperature for 18 hours. The THF was evaporated. Everything was dissolved in 250 mL chloroform and washed successively with H$_2$O, 1N NaHCO$_3$, brine. The resulting solution was dried with NaSO$_4$ and evaporated to dryness. 3 was obtained as a slightly coloured yellow oil.
$^1$H-NMR (300 MHz, CDCl$_3$, 22° C., TMS): δ (ppm)=6.5- 6.0 (6H, CH, acrylate), 5.25-5.18 (m, 9.1H, CH(lac)); 4.83- 4.74 (m, 15.9H, CH$_2$(gly)); 4.30 (m, 4H, —(C=O) OCH$_2$CH$_2$O—, —O(C=O)CH$_2$OH, —O(C=O)CH(CH$_3$) OH); 3.70 (m, 4H, —(C=O)OCH$_2$CH$_2$O—); 1.58 (m, 30H, CH$_3$(lac))

Synthesis of p-(Lactide-co-Caprolactone)1000 diol (4)

dl-Lactide (37.41 g, 25.95 mmol), ε-caprolactone (29.63 g, 25.9 mmol) and diethyleneglycol (7.959 g, 75 mmol) were melted at 150° C. Tin(II)-ethylhexanoate (21 mg) was added as a catalyst. The reaction was allowed to proceed for 18 h upon which the reaction mixture was cooled to room temperature to obtain 4.
$^1$H-NMR (300 MHz, CDCl$_3$, 22° C., TMS): δ (ppm)= 5.25-5.18 (m, 5H, CH(lac)); 4.40-4.4 (m, 10H, CH$_2$(cap)); 4.30 (m, 4H, —(C=O)OCH$_2$CH$_2$O—, —O(C=O)CH$_2$OH, —O(C=O)CH(CH$_3$)OH); 3.70 (m, 4H, —(C=O) OCH$_2$CH$_2$O—); 3.4 (broad, 2H, —OH); 2.4 (m, CH$_2$ (cap) 1.58 (m, CH$_3$(lac) and CH$_2$(cap))

Synthesis of p-(Lactide-co-Caprolactone)1000-(t-Bu-LDI-HEA)$_2$ (5)

Hydroxyethylacrylate (2.23 g, 20 mmol) was added dropwise to a solution of L-lysine-diisocyanate tert-butylester (tert.-butyl-LDI) (5.08 g, 20 mol), tin-(II)-ethylhexanoate (0.023 g, 0.056 mmol), Irganox 1035 (0.023 g) in toluene (17.4 gram) and dry air at controlled temperature (<20° C.). The reaction was monitored with GPC w.r.t to the presence of HEA. After 18 hours 4 (10 gram, 5 mmol) was added at room temperature. The temperature was gradually increased till 60° C. until the IR vibrational stretch of NCO group at v=2260 cm$^{-1}$ disappeared. When the reaction was complete, based on IR spectroscopy the solvent was evaporated. 5 was obtained without further purification as a slightly colored yellow oil.
$^1$H-NMR (300 MHz, CDCl$_3$, 22° C., TMS): δ (ppm)=6.5- 6.0 (6H, CH, acrylate), 5.5 (2H, NHCO), 5.3 (2H, NHCO); 5.25-5.18 (m, H, CH(lac)); 4.40 (m, 10H, CH$_2$(cap)); 4.30 (m, 6.7H, —(C=O)OCH$_2$CH$_2$O—, —O(C=O)CH$_2$OH, —O(C=O)CH(CH$_3$)OH); 4.3-4.1 (m, CH$_2$, CH (Lys), and CH$_2$, HEA); 3.70 (m, 4H, —(C=O)OCH$_2$CH$_2$O—); 3.1 (m, 4H, Lys); 2.4 (m, CH$_2$ (cap) 1.58 (m, CH$_3$(lac) and CH$_2$ (cap)); 1.8-1.3 (8H, Lys, 12H, t-Butylester, m, 4H, CH$_2$ (Lys)) 1.58 (m, 19.1H, CH$_3$(lac))

Synthesis of p-(lactide-co-glycolide)1500 triol (6)

Trimethylolpropane (10 gram) was recrystalised in ethylacetate (25 mL) to dry the sample. dl-Lactide (25.22 g, 17.5 mmol), glycolide (20.31 g, 17.5 mmol) and trimethylolpropane (4.47 g, 33.3 mmol) were melted at 150° C. Tin(II)- ethylhexanoate (14 mg) was added as a catalyst. The reaction was allowed to proceed for 18 h upon which the reaction mixture was cooled to room temperature to obtain 6.
$^1$H-NMR (300 MHz, CDCl$_3$, 22° C., TMS): δ (ppm)=5.4- 5.0 (m, 8.2, CH(lac)); 4.82-4.70 (m, 16.9H, CH$_2$(gly)); 4.5-4.0 (m, 9.0H, —O(C=O)CH$_2$OH, —O(C=O)CH (CH$_3$)OH) and CH$_3$CH$_2$C(CH$_2$O—)$_3$); 3.0 (broad, 3H, —OH); 1.57 (m, 31.6H, CH$_3$(lac) and CH$_3$CH$_2$C(CH$_2$ O—)$_3$); 0.90 (t, 3H, CH$_3$CH$_2$C(CH$_2$O—)$_3$)

Synthesis of p-(Lactide-co-Glycolide)1500 triacrylate (7)

6 (10 gram, 6.6 mmol) and triethylamine (0.71 gram, 7 mmol) were dissolved THF (100 mL). Acryloylchloride (0.67 g, 7 mmol) dissolved in THF (25 mL) was added dropwise at controlled temperature (<5° C.). The reaction mixture was stirred at room temperature for 18 hours. The THF solvent was evaporated. The residue was dissolved in 250 mL chloroform and washed successively with H$_2$O, 0.1

N NaHCO$_3$, brine. The resulting solution was dried with NaSO$_4$ and evaporated to dryness. 7 was obtained as a slightly colored yellow oil.

$^1$H-NMR (300 MHz, CDCl$_3$, 22° C., TMS): δ (ppm)=6.5-6.0 (6H, CH, acrylate), 5.4-5.0 (m, 8.2, CH(lac)); 4.82-4.70 (m, 16.9H, CH$_2$(gly)); 4.5-4.0 (m, 9.0H, —O(C═O)CH$_2$OH, —O(C═O)CH(CH$_3$)OH) and CH$_3$CH$_2$C(CH$_2$O—)$_3$); 3.0 (broad, 3H, —OH); 1.57 (m, 31.6H, CH$_3$ (lac) and CH$_3$CH$_2$C(CH$_2$O—)$_3$); 0.90 (t, 3H, CH$_3$CH$_2$C(CH$_2$O—)$_3$)

Synthesis of p-(Lactide-co-Glycolide)1500-(t-Bu-LDI-HEA)$_3$ (8)

Hydroxyethylacrylate (1.16 g, 10 mmol) was added dropwise to a solution of L-lysine-diisocyanate tert-butylester (2.54 g, 10 mol), Tin-(II)-ethylhexanoate (0.037 g, 0.084 mmol), Irganox 1035 (0.012 g) in tetrahydrofuran (17.4 gram) and dry air at controlled temperature (<20° C.). The reaction was monitored with GPC w.r.t to the presence of HEA. After 72 hours 6 (10 gram, 5 mmol) was added at room temperature. The temperature was gradually increased till 60° C. until the IR vibrational stretch of NCO group at v=2260 cm$^{-1}$ disappeared. When the reaction was complete, based on IR spectroscopy the solvent was evaporated. 8 was obtained without further purification as a slightly colloured yellow oil.

$^1$H-NMR (300 MHz, CDCl$_3$, 22° C., TMS): δ (ppm)=6.5-6.0 (6H, CH, acrylate), 5.5 (2H, NHCO), 5.3 (2H, NHCO); 5.4-5.0 (m, 8.2, CH(lac)); 4.82-4.70 (m, 16.9H, CH$_2$(gly)); 4.5-4.0 (m, 9.0H, —O(C═O)CH$_2$OH, —O(C═O)CH(CH$_3$)OH) and CH$_3$CH$_2$C(CH$_2$O—)$_3$); 4.3-4.1 (m, CH$_2$, CH (Lys), and CH$_2$, HEA); 3.70 (m, 4H, —(C═O)OCH$_2$CH$_2$O—); 3.1 (m, 6H, Lys); 1.8-1.3 (12H, Lys, 18H, t-Butylester, m, 6H, CH$_2$ (Lys)) 1.58 (m, 19.1H, CH$_3$(lac))

Synthesis of PEG600-(t-Bu-LDI-HEA)$_2$ (9)

Hydroxyethylacrylate (4.8 g, 40 mmol) was added dropwise to a solution of the L-lysine-diisocyanate tert-butylester (10.2 g, 40 mmol), tin-(II)-ehtylhexanote (50 mg) and Irganox 1035 (50 mg) at controlled temperature (<20° C.). The reaction was monitored with GPC w.r.t to the presence of HEA. After 18 hours Polyethyleneglycol Mn=600 (12 gram, 20 mmol) was added at room temperature. The temperature was gradually increased till 60° C. until the IR vibrational stretch of NCO group at v=2260 cm$^{-1}$ disappeared. When the reaction was complete, based on IR spectroscopy the solvent was evaporated. 9 was obtained without further purification as a slightly coloured yellow oil.

$^1$H-NMR (300 MHz, CDCl$_3$, 22° C., TMS): δ (ppm)=6.5-6.0 (6H, CH, acrylate), 5.5 (2H, NHCO), 5.3 (2H, NHCO), 4.3-4.1 (m, CH$_2$, CH (Lys), and CH$_2$, HEA) and (m, 4H, —(C═O)OCH$_2$CH$_2$O—, 3.6 (s, CH$_2$, PEG600 and (m, 4H, —(C═O)OCH$_2$CH$_2$O—); 3.1 (m, 4H, Lys), 1.8-1.3 (8H, Lys, 12H, t-Butylester, m, 4H, CH$_2$ (Lys))

Synthesis of p-(Lactide-co-Glycolide)1000-(m-LDI-HEA)$_2$ (10)

Hydroxyethylacrylate (HEA, 6.0 g, 50 mmol) was added dropwise to a solution of L-lysine-diisocyanate methylester (Me-LDI) (10.6 g, 50 mmol), Tin-(II)-ethylhexanoate (0.020 g, 0.050 mmol), Irganox 1035 (0.060 g) in Tetrahydrofuran (100 mL) and dry air at controlled temperature (<20° C.). The reaction was monitored with GPC w.r.t to the presence of HEA. After 18 hours 1 (25 gram, 25 mmol) was added at room temperature. The temperature was gradually increased until the IR vibrational stretch of NCO group at v=2260 cm$^{-1}$ disappeared. When the reaction was complete, based on IR spectroscopy the solvent was evaporated. 10 was obtained without further purification as a slightly colloured yellow oil.

$^1$H-NMR (300 MHz, CDCl$_3$, 22° C., TMS): δ (ppm)=6.5-6.0 (6H, CH, acrylate), 5.5 (2H, NHCO), 5.3 (2H, NHCO); 5.25-5.18 (m, H, CH(lac)); 4.83-4.74 (m, 2H, CH$_2$(gly)); 4.30 (m, 6.7H, —(C═O)OCH$_2$CH$_2$O—, —O(C═O)CH$_2$OH, —O(C═O)CH(CH$_3$)OH); 4.3-4.1 (m, CH$_2$, CH (Lys), and CH$_2$, HEA); 3.70 (m, 4H, —(C═O)OCH$_2$CH$_2$O— and 3H, methylester); 3.2 (m, 4H, Lys); 1.8-1.3 (8H, Lys, m, 4H, CH$_2$ (Lys)) 1.58 (m, 19.1H, CH$_3$(lac))

Synthesis of p-(Lactide-co-Caprolactone)1545 diol (11)

dl-Lactide (51.9 g, 36.1 mmol), ε-caprolactone (41.2 g, 36.1 mmol) and diethyleneglycol (6.846 g, 64 mmol) were melted at 150° C. Tin(II)-ethylhexanoate (29 mg) was added as a catalyst. The reaction was allowed to proceed for 18 h upon which the reaction mixture was cooled to room temperature to obtain 11.

$^1$H-NMR (300 MHz, CDCl$_3$, 22° C., TMS): δ (ppm) =5.25-5.18 (m, 5H, CH(lac)); 4.40-4.4 (m, 10H, CH$_2$(cap)); 4.30 (m, 4H, —(C═O)OCH$_2$CH$_2$O—, —O(C═O)CH$_2$OH, —O(C═O)CH(CH$_3$)OH); 3.70 (m, 4H, —(C═O)OCH$_2$CH$_2$O—); 3.4 (broad, 2H, —OH); 2.4 (m, CH$_2$ (cap) 1.58 (m, CH$_3$(lac) and CH$_2$(cap))

Synthesis of p-(Lactide-co-Caprolactone)1545 diacrylate (12)

11 (100 gram, 64.7 mmol) and triethyleneamine (14.36 g, 0.142 mol) was dissolved in 100 mL tetrahydrofuran. Acryloylchloride (12.8 g, 0.141 mol) dissolved in THF (50 mL) was added dropwise to the solution at controlled temperature (<5° C.). The reaction mixture was stirred at room temperature for 18 hours. The THF was evaporated. Everything was dissolved in 250 mL chloroform and washed successively with H$_2$O, 1N NaHCO$_3$, brine. The resulting solution was dried with NaSO$_4$ and evaporated to dryness. 12 was obtained as a slightly coloured yellow oil.

$^1$H-NMR (300 MHz, CDCl$_3$, 22° C., TMS): δ (ppm)=6.5-6.0 (6H, CH, acrylate), 5.25-5.18 (m, 5H, CH(lac)); 4.40-4.4 (m, 10H, CH$_2$(cap)); 4.30 (m, 4H, —(C═O)OCH$_2$CH$_2$O—, —O(C═O)CH$_2$OH, —O(C═O)CH(CH$_3$)OH); 3.70 (m, 4H, —(C═O)OCH$_2$CH$_2$O—); 3.4 (broad, 2H, —OH); 2.4 (m, CH$_2$ (cap) 1.58 (m, CH$_3$(lac) and CH$_2$(cap))

Synthesis of p-(Lactide-co-Caprolactone)1000-(m-LDI-HEA)$_2$ (13)

Hydroxyethylacrylate (6.0 g, 50 mmol) dissolved in 25 mL THF was added dropwise to a solution of L-lysine-diisocyanate methylester (10.6 g, 50 mol), Tin-(II)-ethylhexanoate (0.021 g, 0.050 mmol), Irganox 1035 (0.060 g) in tetrahydrofuran (50 mL) and dry air at controlled temperature (<20° C.). The reaction was monitored with GPC w.r.t to the presence of HEA. After 18 hours 4 (25 gram, 25 mmol) dissolved in 50 mL. Tetrahydrofuran was added at room temperature. The temperature was gradually increased till 60° C. until the IR vibrational stretch of NCO group at v=2260 cm$^{-1}$ disappeared. When the reaction was complete, based on IR spectroscopy the solvent was evaporated. 13 was obtained without further purification as a slightly colloured yellow oil.

$^1$H-NMR (300 MHz, CDCl$_3$, 22° C., TMS): δ (ppm)=6.5-6.0 (6H, CH, acrylate), 5.5 (2H, NHCO), 5.3 (2H, NHCO); 5.25-5.18 (m, H, CH(lac)); 4.40 (m, 10H, CH$_2$(cap)); 4.30 (m, 6.7H, —(C═O)OCH$_2$CH$_2$O—, —O(C═O)CH$_2$OH, —O(C=O)CH(CH₃)OH); 4.3-4.1 (m, CH (Lys), and CH₂, HEA); 3.70 (m, 4H, —(C=O)OCH₂CH₂O—); 3.1 (m, 4H, Lys and 3H, methylester); 2.4 (m, CH₂ (cap) 1.58 (m, CH₃(lac) and CH₂(cap)); 1.8-1.3 (8H, Lys, m, 4H, CH₂ (Lys)) 1.58 (m, 19.1H, CH₃(lac))

Synthesis of t-Bu-LDI-(HEA)₂ (14)

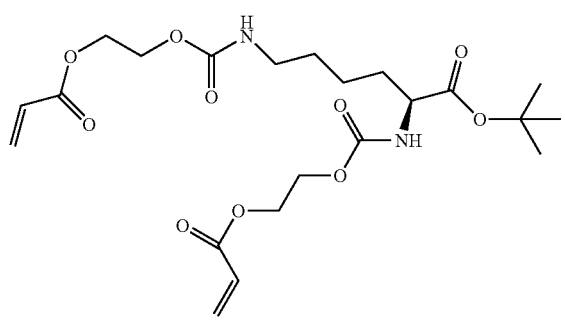

Hydroxyethylacrylate (HEA, 9.13 g, 78 mmol) dissolved in toluene (15 mL) was added dropwise under a dry atmosphere to a solution of L-lysine-diisocyanate tert-butylester (10 g, 39 mmol), tin-(II)-ethylhexanoate (0.086 g), Irganox 1035 (89 mg) in toluene (50 mL) at controlled temperature (<5° C.). The temperature was gradually increased till 60° C. until the IR vibrational stretch of NCO group at v=2260 cm⁻¹ disappeared. When the reaction was complete, based on IR spectroscopy the solvent was evaporated. 14 was obtained without further purification as a colourless oil.

¹H-NMR (300 MHz, CDCl₃, 22° C., TMS): δ 6.5-6.0 (6H, CH, acrylate), 5.4 (2H, NHCO), 4.9 (2H, NHCO); 4.4 (m, CH₂, HEA); 4.3 (m, CH (Lys),); 3.1 (m, 4H, Lys); 1.8-1.3 (6H, CH₂, Lys and 12H, t-Butylester).

Synthesis of LDI-(HEA)₂ (15)

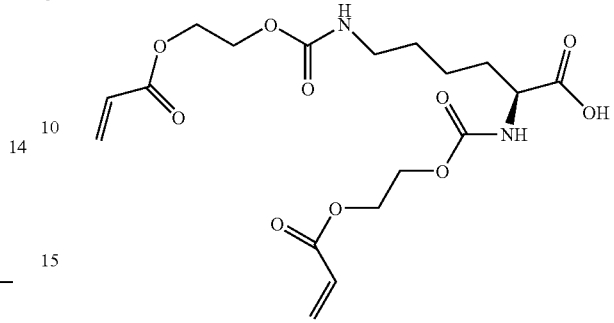

14 (18.3 gram, 37.6 mmol), trifluoroacetic acid (TFA, 36 gram) and dichloromethane (10 g) were stirred at 35° C. for 18 h. The deprotection reaction was complete based on ¹H NMR (disappearance tort-butyl ester at 1.39 ppm). The reaction mixture was dissolved in 250 mL dichloromethane and 200 mL of water. While stirring, the mixture was brought to pH=2 with aq. 1N NaHCO₃ solution. The CH₂Cl₂ layer was washed 6 times with 200 mL water; during each extraction to pH was brought to 2 using aq. 1N NaHCO₃ solution. The organic phase was concentrated in vacuo to give 15 as a colourless oil. The TFA had been completely removed as confirmed by F-NMR (internal standard 4,4'-difluorobenzophenone).

¹H-NMR (300 MHz, CDCl₃, 22° C., TMS): δ 6.5-6.0 (6H, CH, acrylate), 5.4 (2H, NHCO), 4.9 (2H, NHCO); 4.4 (m, CH₂, HEA, and m, CH (Lys),); 3.1 (m, 4H, Lys); 1.8-1.3 (6H, CH₂, Lys).

Synthesis of LDI-(HEA)₂-Arg(Pmc)-Gly-Asp (O^tBu)-O^tBu (16)

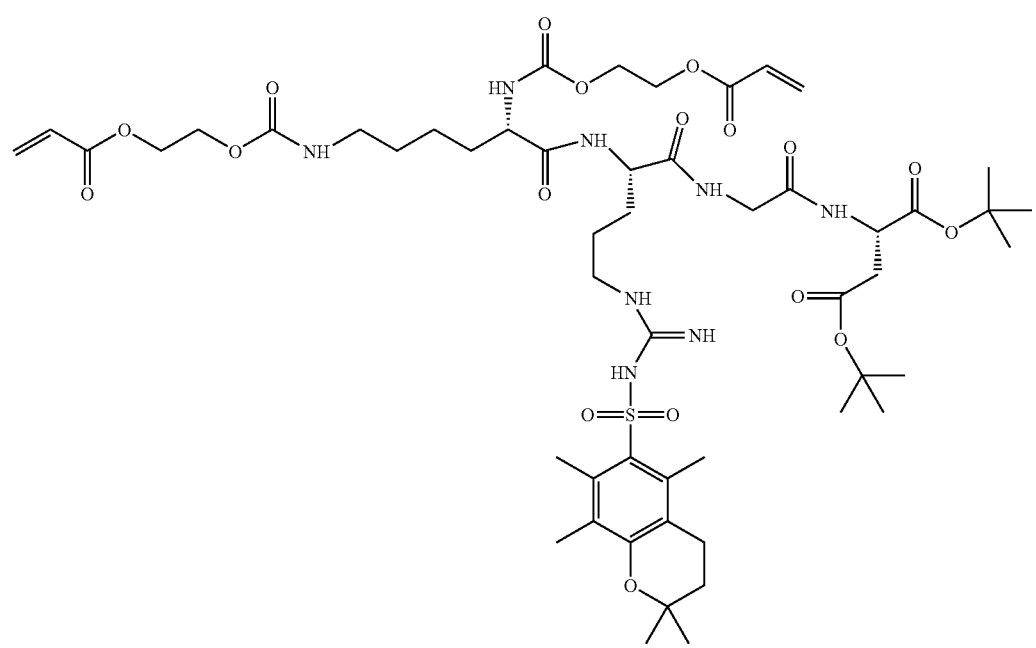

Diisopropylethylamine (0.125 g, 0.97 mmol) was added to a solution of 15 (0.379 g, 0.88 mmol) in dichloromethane (22 mL) at 0° C. Successively, 1-hydroxy-7-azabenzotriazole, (0.131 g, 0.97 mmol), N-(3-dimethylaminopropyl)-N'-ethylcarbodiimide hydrochloride (0.186 g, 0.97 mmol) and Arg(Pmc)-Gly-Asp(O$^t$Bu)-O$^t$Bu (0.702 g, 0.97 mmol) were added and the reaction mixture was stirred for 1 h at 0° C. and 17 h at ambient temperature. The mixture was concentrated under reduced pressure and the resulting residue taken up in 105 mL EtOAc, washed with aq. HCl (pH=2.5, 3×100 mL), saturated eq. NaHCO$_3$ (2×100 mL) and brine (100 mL). The organic phase was dried (Na$_2$SO$_4$) and evaporated to dryness. 16 was obtained in impure form as a white solid in a yield of 85% based on 15. The solid was purified by column chromatography on silica using EtOAc/MeOH (95/5, v/v) as the eluent giving pure 16 as a white powder in 53% yield based on 15.

$^1$H-NMR (300 MHz, CDCl$_3$): δ (ppm) 7.8-7.25 (3H, m, arom. Pmc), 6.32 (3H, m, acryloyl+NH), 6.08 (3H, m, acryloyl+NH), 5.74 (2H, d, acryloyl), 4.61 (1H, m, C$^α$-Arg or C$^α$-Asp or C$^α$-Lys), 4.49 (1H, m, C$^α$-Arg or C$^α$-Asp or C$^α$-Lys), 4.23 (9H, 2×CH$_2$CH$_2$ HEA, C$^α$-Arg or C$^α$-Asp or C$^α$-Lys), 3.92 (2H, s, CH$_2$-Gly), 3.33 (2H, m, CH$_2$—N$^ε$-Lys or C$\underline{H}_2$—C(NH$_2$)=NH), 3.07 (2H, m, CH$_2$—N$^ε$-Lys or C$\underline{H}_2$—C(NH$_2$)=NH), 2.90-1.50 (25H, m, CH$_2$-Asp, CH$_2$—CH$_2$-Arg, CH$_2$—CH$_2$—CH$_2$-Lys, 3×CH$_3$ Pmc, CH$_2$CH$_2$ Pmc), 1.35 (18H, s, 6×CH$_3$ tBu), 1.20 (6H, s, C(CH$_3$)$_2$ Pmc). HPLC-MS: [M+H]$^+$=1138 (as calculated).

Synthesis of LDI-(HEA)$_2$-Arg-Gly-Asp (17)

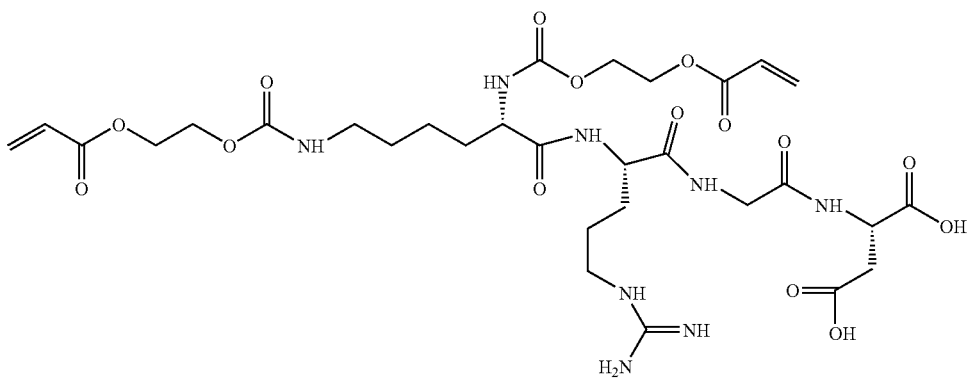

17

16 (3.45 g, 3.03 mmol) was charged in a Schlenck reactor under a nitrogen atmosphere and the reactor was brought under reduced pressure and flushed five times with nitrogen. Subsequently, trifluoroacetic acid (95 mL) was dosed under a nitrogen atmosphere. After 30 min an aliquot was withdrawn from the reaction mixture and analyzed with HPLC indicating complete deprotection. The TFA was removed under reduced pressure and the product was precipitated and thoroughly washed with anhydrous diethyl ether. The product was dried on the air giving 2.25 g of pure 17 as a white solid (98% yield based on 16).

$^1$H-NMR (300 MHz, MeOD): δ (ppm) 6.43 (2H, d, acryloyl), 6.23 (1H, d, acryloyl), 6.17 (1H, d, acryloyl), 5.91 (2H, d, acryloyl), 4.8 (2H, m, C$^α$-Arg/C$^α$-Asp), 4.5-4.2 (9H, 2×CH$_2$CH$_2$ HEA, C$^α$-Lys), 3.93 (2H, s, CH$_2$-Gly), 3.23 (2H, m, CH$_2$—N$^E$-Lys), 3.11 (2H, m, C$\underline{H}_2$—C(NH$_2$)=NH), 2.90 (2H, d, CH$_2$-Asp), 2.05-1.15 (10H, CH$_2$—CH$_2$-Arg, CH$_2$—CH$_2$—CH$_2$-Lys). HPLC-MS: [M+H]$^+$=759 (as calculated).

Synthesis of
H-Arg(Pmc)-OtBu-HEA-6-amino-hexanoate (18)

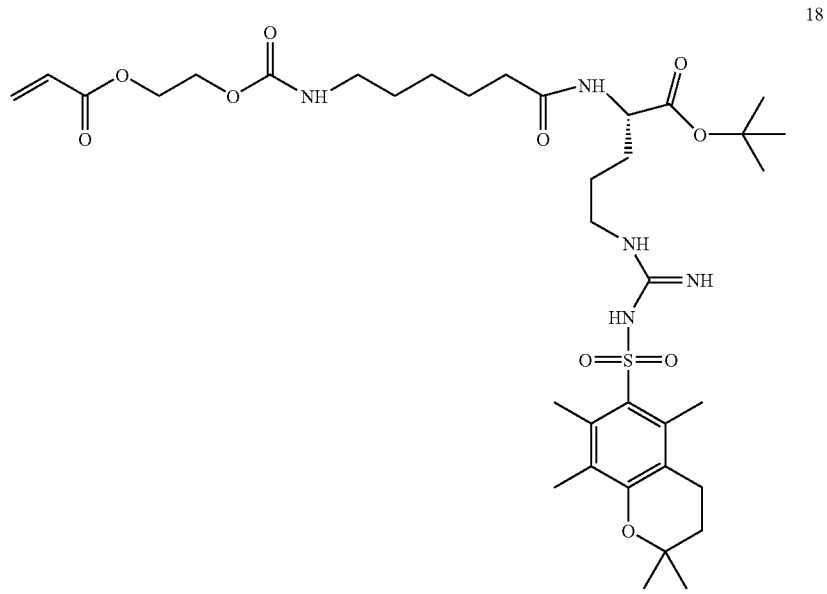 [SMILES: C=CC(=O)OCCOC(=O)NCCCCCC(=O)N[C@@H](CCCNC(=N)NS(=O)(=O)c1c(C)c(C)c2c(c1C)CCC(C)(C)O2)C(=O)OC(C)(C)C]

To a solution of 571 mg (2.09 mmol) of HEA-6-amino-hexanoate in 22 mL dichloromethane at 0° C. were added N-(3-dimethylaminopropyl)-N'-ethylcarbodiimide.HCl (441 mg, 2.30 mmol), 1-hydroxy-7-azabenzotriazole (313 mg, 2.30 mmol), N,N-diisopropylethylamine (384 μl, 2.30 mmol), Arg-(Pmc)-OtBu (1.093 g, 2.20 mmol) in this order. The reaction mixture was stirred overnight at ambient temperature and subsequently diluted with 100 mL of EtOAc and washed with aq. HCl (0.5 M, 3×25 mL) and brine (2×25 mL). The organic layer was dried with $Na_2SO_4$ and concentrated in vacuo. The product was purified by column chromatography on silica gel using EtOAc/n-heptane (33%→0% n-heptane) as the eluent. This yielded (18) as a white solid (0.437 g, 0.58 mmol).

$^1$H NMR (CDCl$_3$, 300 MHz) δ 6.48 (dd, J=17.2 and 1.4 Hz, 1H), 6.27 (d, J=8.1 Hz, 1H), 6.12 (dd, J=17.1 and 10.6 Hz, 1H), 6.13-6.09 (m, 1H), 5.85 (dd, J=10.4 and 1.4 Hz, 1H), 4.95 (t, J=5.2 Hz, 1H), 4.48-4.37 (m, 1H), 4.35-4.25 (m, 4H), 3.32-3.11 (bs, 2H), 3.14 (q, J=6.62 Hz, 2H), 2.62 (t, J=6.9 Hz, 2H), 2.58 (s, 3H), 2.57 (s, 3H), 2.28-2.15 (m, 2H), 2.10 (s, 3H), 1.78 (t, J=6.9 Hz, 2H), 1.68-1.48 (m, 12H), 1.46 (s, 9H), 1.29 (s, 6H)

Synthesis of H-Arg(Pmc)-OtBu-LDI-(HEA)₂ (19)

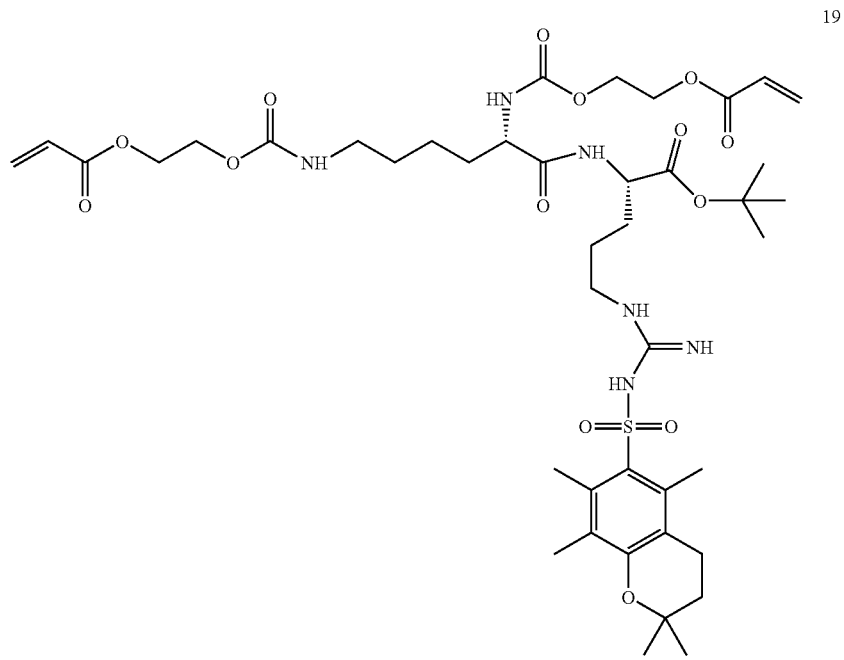 [SMILES: C=CC(=O)OCCOC(=O)NCCCC[C@H](NC(=O)OCCOC(=O)C=C)C(=O)N[C@@H](CCCNC(=N)NS(=O)(=O)c1c(C)c(C)c2c(c1C)CCC(C)(C)O2)C(=O)OC(C)(C)C]

To a solution of 1.24 g (2.88 mmol) of LDI-(HEA)₂ in 30 mL dichloromethane at 0° C. were added N-(3-dimethylaminopropyl)-N'-ethylcarbodiimide.HCl (608 mg, 3.17 mmol), 1-hydroxy-7-azabenzotriazole (439 mg, 3.17 mmol), N,N-Diisopropylethylamine (532 μl, 3.17 mmol), Arg-(Pmc)-OtBu (1.53 g, 3.02 mmol) in this order. The reaction mixture was stirred overnight at ambient temperature, diluted with 100 mL of EtOAc and washed with aq. HCl (0.5 M, 3×30 mL) and brine (2×30 mL). The organic layer was dried (Na₂SO₄) and concentrated in vacuo. The product was purified by column chromatography on silica gel using EtOAc/n-heptane (33%→0% n-heptane) as the eluent. This yielded (19) as a white solid (2.0 g, 2.21 mmol).

¹H NMR (CDCl₃, 300 MHz) δ 7.08 (d, J=7.3 Hz, 1H), 6.42 (d, J=17.2 Hz, 2H), 6.13 (dd, J=10.3 and 17.2 Hz, 2H), 6.05-5.96 (m, 1H), 5.85 (d, J=10.6 Hz, 2H), 5.81-5.76 (m, 1H), 5.13 (t, J=5.3 Hz, 1H), 4.47-4.44 (m, 1H), 4.37-4.24 (m, 8H), 4.23-4.13 (m, 1H), 3.26-3.11 (m, 4H), 2.62 (t, J=6.9 Hz, 2H), 2.57 (s, 3H), 2.55 (s, 3H), 2.10 (2, 3H), 1.79 (t, J=6.8 Hz, 2H), 1.87-1.35 (m, 12H), 1.44 (s, 9H), 1.30 (s, 6H).

Synthesis of p-(lactide-co-glycolide)1550 diol (20)

dl-Lactide (51.6 g, 0.358 mol), glycolide (41.5 g, 0.358 mmol) and diethyleneglycol (6.85 g, 6.45 mmol) were melted at 150° C. Tin(II)-ethylhexanoate (29 mg) was added as a catalyst. The reaction was allowed to proceed for 18 h upon which the reaction mixture was cooled to room temperature to obtain 20.

¹H-NMR (300 MHz, CDCl₃, 22° C., TMS): δ (ppm)= 5.25-5.18 (m, 5.3H, CH(lac)); 4.83-4.74 (m, 10.6H, CH₂(gly)); 4.30 (m, 6.7H, —(C=O)OCH₂CH₂O—, —O(C=O)CH₂OH, —O(C=O)CH(CH₃)OH); 3.70 (m, 4H, —(C=O)OCH₂CH₂O—); 2.79 (broad, 2H, —OH); 1.58 (m, 19.1H, CH₃(lac))

Synthesis of p-(Lactide-co-Glycolide)1550 diacrylate (21)

20 (100 gram, 65 mmol) and triethyleneamine (14.36 g, 0.141 mol) was dissolved in 100 mL tetrahydrofuran. Acryloylchloride (12.8 g, 0.141 mol) dissolved in THF (50 mL) was added dropwise to the solution at controlled temperature (<5° C.). The reaction mixture was stirred at room temperature for 18 hours. The THF was evaporated. Everything was squenched in 2500 mL ethylacetate. The triethylamine.HCl salt precipitated well. This was isolated via filtration. The ethylacetate layer was washed successively with 2 times 150 mL brine, 150 mL NaHCO₃, and 2 times 150 mL water. The resulting solution was dried with NaSO₄ and evaporated to dryness. 21 was obtained as a slightly coloured yellow oil.

¹H-NMR (300 MHz, CDCl₃, 22° C., TMS): δ (ppm)=6.5-6.0 (6H, CH, acrylate), 5.25-5.18 (m, 9.1H, CH(lac)); 4.83-4.74 (m, 15.9H, CH₂(gly)); 4.30 (m, 4H, —(C=O)OCH₂CH₂O—, —O(C=O)CH₂OH, —O(C=O)CH(CH₃)OH); 3.70 (m, 4H, —(C=O)OCH₂CH₂O—); 1.58 (m, 30H, CH₃(lac))

Synthesis of p-(Glycolide-co-Caprolacton)1000-(m-LDI-HEA)₂ (22)

Hydroxyethylacrylate (HEA, 6 g, 50 mmol) was added dropwise to a solution of L-lysine-diisocyanate methylester (10.6 g, 50 mmol), Tin-(II)-ethylhexanoate (0.020 g, 0.049 mmol), Irganox 1035 (0.060 g) in THF (50 mL) and dry air at controlled temperature (<20° C.). The reaction was monitored with GPC w.r.t to the presence of HEA. After 18 hours p-(glycolide-co-Caprolacton) 1000-diol (25 gram, 25 mmol) dissolved THF (50 mL) was added at room temperature. The temperature was gradually increased till 60° C. until the IR vibrational stretch of NCO group at v=2260 cm⁻¹ disappeared. When the reaction was complete, based on IR spectroscopy the solvent was evaporated. 22 was obtained without further purification as a slightly coloured yellow oil.

$^1$H-NMR (300 MHz, CDCl$_3$, 22° C., TMS): δ (ppm)=6.5-6.0 (6H, CH, acrylate), 5.6 (2H, NHCO), 5.4 (2H, NHCO); 4.7 (m, 2H, CH$_2$(gly)); 4.6 (m, 10H, CH$_2$(cap)); 4.30 (m, H, —(C=O)OCH$_2$CH$_2$O—, —O(C=O)CH$_2$OH, —O(C=O) CH(CH$_3$)OH); 4.1 (m, CH$_2$, CH (Lys), and CH$_2$, HEA); 3.70 (m, 4H, —(C=O)OCH$_2$CH$_2$O— and 3H, methylester)); 3.1 (m, 4H, Lys); 2.4 (m, CH$_2$ (cap)); 1.8-1.3 ((CH$_2$(cap)); m, 8H, CH$_2$ (Lys))

Synthesis of p-(Glycolide-co-caprolactone)1550 diol (23)

Caprolactone (46.2 g, 0.41 mol), glycolide (46.9 g, 0.41 mol) and diethyleneglycol (6.846 g, 64.5 mmol) were melted at 150° C. Tin(II)-ethylhexanoate (32.8 mg) was added as a catalyst. The reaction was allowed to proceed for 18 h upon which the reaction mixture was cooled to room temperature to obtain 23.

$^1$H-NMR (300 MHz, CDCl$_3$, 22° C., TMS): δ (ppm)=4.7 (m, 2H, CH$_2$(gly)); 4.6 (m, 10H, CH$_2$(cap)); 4.30 (m, H, —(C=O)OCH$_2$CH$_2$O—, —O(C=O)CH$_2$OH, —O(C=O) CH(CH$_3$)OH); 4.1 CH$_2$, HEA); 3.70 (m, 4H, —(C=O) OCH$_2$CH$_2$O—); 2.4 (m, CH$_2$ (cap)); 1.8-1.3 ((CH$_2$(cap))

Synthesis of p-(Glycolide-co-caprolactone)1550-diacrylate (24)

24 (100 gram, 65 mmol) and triethyleneamine (14.36 g, 0.141 mol) was dissolved in 100 mL tetrahydrofuran. Acryloylchloride (12.8 g, 0.141 mol) dissolved in THF (50 mL) was added dropwise to the solution at controlled temperature (<5° C.). The reaction mixture was stirred at room temperature for 18 hours. The THF was evaporated. Everything was squenched in 2500 mL ethylacetate. The triethylamine.HCl salt was removed via decantation. The ethylacetate layer was washed successively with 250 mL brine, 250 mL NaHCO$_3$, and 250 mL water. The resulting solution was dried with NaSO$_4$ and evaporated to dryness. 24 was obtained as a slightly colored yellow oil.

$^1$H-NMR (300 MHz, CDCl$_3$, 22° C., TMS): δ (ppm)=6.5-5.8 (6H, CH, acrylate), 4.7 (m, 2H, CH$_2$(gly)); 4.6 (m, 10H, CH$_2$(cap)); 4.30 (m, H, —(C=O)OCH$_2$CH$_2$O—, —O(C=O)CH$_2$OH, —O(C=O)CH(CH$_3$)OH); 4.1 (CH$_2$, HEA); 3.70 (m, 4H, —(C=O)OCH$_2$CH$_2$O—); 2.4 (m, CH$_2$ (cap)); 1.8-1.3 ((CH$_2$(cap))

Synthesis of (MeO-PEG750)$_2$-m-Lys (25)

L-lysine-diisocyanate methylester (1.5 g), Irganox1035 (2 mg) and Tin(II) ethylhexanoate were dissolved in dry toluene (5 mL). To this mixture MeO-PEG750-OH (10.9 g) in 10 mL toluene was added drop wise until on IR λ=2243 cm$^{-1}$ disappeared. When the reaction was complete, based on IR spectroscopy the solvent was evaporated. 25 was obtained without further purification (10.81 g).

$^1$H NMR (400 MHz, CDCl$_3$) δ; 1.0-1.8 (m, 6H, CH$_2$ (Lys)), 3.1-3.2 (m, 2H, CH$_2$ (Lys)), 3.4 (s, 6H, OMe (Peg)), 3.5-3.8 (m, 126H, CH$_2$ (Peg), OMe (Lys), 4.2 (m, 4H, (2×) CH$_2$—OMe (Peg)), 4.3 (m, 1H, αH) 4.9 (m, 1H, NH), 5.4 (d, 1H NH).

$^{13}$CNMR (75.5 MHz, CDCl$_3$) δ; 22.0, 28.9, 31.3, 39.9, 51.5, 51.7, 53.3, 58.4, 60.9, 63.1, 63.6, 68.8, 69.0, 69.6, 69.8, 71.3, 72.1, 155.2, 155.8, 171.9

Synthesis of (MeO-PEG750)$_2$-Lys (26)

25 (9.81 g) was dissolved in 10 mL dioxane. To this solution 7.1 mL 1M NaOH was added. The reaction was complete after stirring at 40° C. for 30 min. according to TLC (5% MeOH/DCM). After stirring the solvent was evaporated in vacuo and the residue was dissolved in water, acidified with 1N HCl and extracted with DCM. The resulting solution was dried (MgSO$_4$) and evaporated to dryness and after column chromatography (5% MeOH/DCM) 26 was obtained as white gel in 90% yield (8.5 g).

$^1$H NMR (400 MHz, CDCl$_3$) δ; 1.0-1.5 (m, 6H, CH$_2$ (Lys)), 2.8 (m, 2H, CH$_2$ (Lys)), 3.0 (s, 6H, OMe (Peg)), 3.3-3.6 (m, 118H, CH$_2$ (Peg), OMe (Lys), 4.0 (m, 5H, (2×) CH$_2$—OMe (Peg) and αH (Lys)), 5.6 (bs, 1H, NH), 5.8 (d, 1H, NH).

$^{13}$C NMR (75.5 MHz, CDCl$_3$) δ; 22.0, 28.9, 31.2, 39.9, 53.0 53.6, 58.4, 60.7, 63.0, 63.4, 68.9, 71.9, 155.2, 155.7, 172.6

Synthesis of Boc-Glycine-o-nitrobenzyl (27)

Boc-Glycine (2 g, 11.4 mmol) was dissolved in 30 mL DCM. DMAP (1.39 g), O-nitrobenzyl alcohol (1.74 g, 11.4 mol and lastly DCC (2.35 g, 11.4 mmol) were added. The reaction was stirred overnight at room temperature. After the precipitate was filtered off the solvent was evaporated in vacuo and re-dissolved in EtOAc. The organic layer was washed successively with 1N KHSO$_4$, H$_2$O, 1N NaHCO$_3$ and brine. The resulting solution was dried (MgSO$_4$) and evaporated to dryness and after column chromatography (1:1 EtOAc/Hexane) 27 was obtained as yellow solid in 98% yield (3.55 g).

$^1$H NMR (300 MHz, CDCl$_3$) δ; 1.2 (s, 9H, Boc), 1.3 (d, 3H, CH$_3$), 4.0 (d, 2H, CH$_2$ (Gly)), 5.0 (bs, 1H, NH), 5.5 (q, 1H, CH (benzyl)), 7.2-7.3 (m, 1H, arom-H), 7.3-7.4 (m, 2H, arom-H), 8.1 (m, 1H, arom-H)

Synthesis of HCl.NH$_2$-Glycine-o-nitrobenzyl (28)

27 was dissolved in EtOAc and an excess of HCl/EtOAc was added. After 2 h of stirring at room temperature the reaction was complete according to TLC. The precipitate 28 was filtrated and washed with ether. Then the filtrate was coevaporated with tert-butanol to eliminate the residual HCl salts.

$^1$H NMR (300 MHz, CDCl$_3$) δ; 1.2 (s, 9H, Boc), 1.3 (d, 3H, CH$_3$), 3.9 (d, 2H, CH$_2$ (Gly)), 5.1 (bs, 1H, NH), 6.4 (q, 1H, CH (benzyl), 7.2-7.3 (m, 1H, arom-H), 7.3-7.4 (m, 2H, arom-H), 8.1 (m, 1H, arom-H)

Synthesis of (MeO-PEG750)$_2$-Lys-Gly-o-nitrobenzyl (29)

26 (400 mg≈0.24 mmol) was dissolved in DMF (2 mL). To this mixture 28 (230 mg) with DIPEA (160 μL) in 3 mL DMF was added followed by the addition of DCC. The reaction was stirred over night at room temperature. Then, 10 mL of DCM was added and the organic layer was successively washed with 1N KHSO$_4$, H$_2$O, 1N NaHCO$_3$ and brine. The resulting solution was dried (MgSO$_4$) and evaporated to dryness and after column chromatography to obtain 29 (5% MeOH/DCM)

$^1$H NMR (300 MHz, CDCl$_3$) δ; 1.0-2.0 (m, 9H, CH$_3$ and CH$_2$ (Lys)), 3.1 (m, 2H, CH$_2$ (Lys)), 3.4 (s, 6H, OMe (PEG)), 3.3-3.9 (m, 120H, CH$_2$ (Peg), OMe (Lys), 4.0-4.4 (m, 7H, (2×) CH$_2$—OMe (Peg), αH (Lys) and CH$_2$ (Gly)), 5.1 (bs, 1H, NH), 5.7 (bs, 1H, NH), 6.2 (m, 1H, CH), 7.0 (bs, 1H, NH), 7.4-7.5 (m, 1H, arom-H), 7.5-7.7 (m, 2H, arom-H), 8.0-8.1 (m, 1H, arom-H)

Synthesis of (MeO-PEG750)$_2$-Lys-Gly (30)

29 (20 mg, 0.01 mmol) was dissolved in MeOH (2 mL) in a reaction tube. While stirring the mixture was exposed to a beam of UV light (254 nm). The reaction was followed with TLC (2:1 EtOAc/Hexane) and after 20 min the reaction was completed. The solvent was evaporated in vacuo and the residue was dissolved in water and washed with EtOAc. Then the water-layer was acidified with 1N HCl and extracted with DCM. The resulting solution was dried (MgSO$_4$), filtered and evaporated to dryness. Compound 30 was obtained as a white gel in quantitative yield (18 mg, 0.01 mmol).

Synthesis of PEG$_{600}$(LDI-HEA)$_2$) with UV Masking Group (32)

The gel (cured PEG$_{600}$(LDI-HEA)$_2$) was dried and weighed (84.1 mg, 0.079 mmol) and put in a syringe with 2 mL of H$_2$O. The syringe was wrapped in aluminium foil to keep the reaction mixture in the dark. 28 (66 mg, 4 eq), DIPEA (54 µl, 4 eq) and EDC (59 mg, 4 eq) were added. After 1 night shaking at room temperature the excess of reagents was washed away with water. After the gel was dried 92.3 mg of gel was obtained in small fragments (92%).

Synthesis of LDI-(HEA)$_2$-Gly-Arg(Pmc)-Gly-Asp (O$^t$Bu)-Ser-(O$^t$Bu)$_2$ (33)

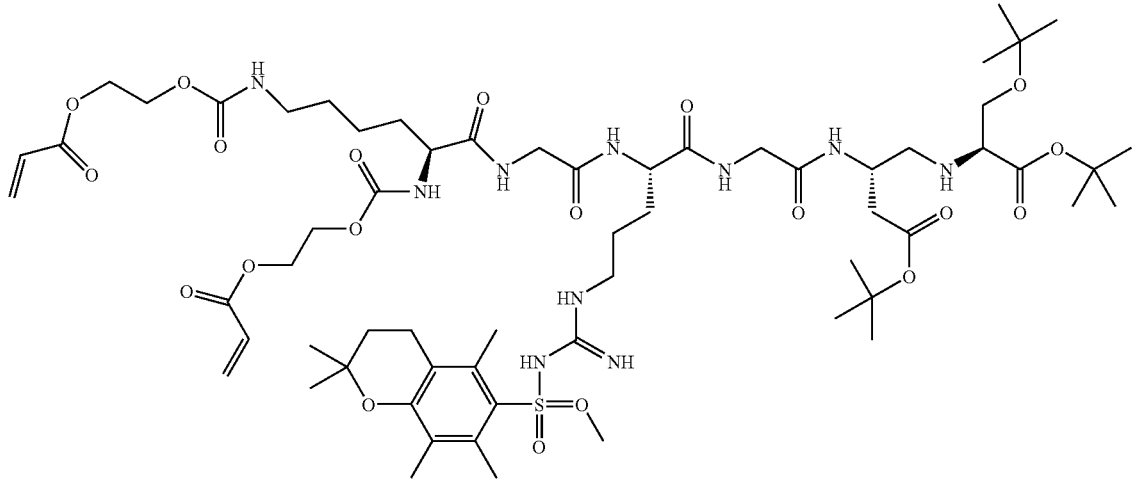

33

$^1$H NMR (300 MHz, CDCl$_3$) δ; 1.0-2.0 (m, 6H, CH$_2$ (Lys)), 3.1 (m, 2H, CH$_2$ (Lys)), 3.4 (s, 6H, OMe (Peg)), 3.3-3.9 (m, 120H, CH$_2$ (Peg), 4.0-4.4 (m, 7H, (2×) CH$_2$—OMe (Peg), αH (Lys) and CH$_2$ (Gly)), 5.5 (bs, 1H, NH), 5.7 (bs, 1H, NH), 7.1 (bs, 1H, NH).

$^{13}$C NMR (75.5 MHz, CDCl$_3$) δ; 21.8, 28.7, 31.5, 39.8, 40.4, 53.2, 54.0, 58.2, 60.7, 62.9, 63.4, 68.6, 69.5, 71.1, 155.2, 155.7, 170.1, 171.6

Synthesis of (MeO-PEG750)$_2$-Lys-Gly-Fmoc-Lys (NH$_3$Cl)—OMe (31)

Compound 30 (50 mg, 0.028) and Fmoc-Lys(NH$_3$Cl)—OMe (43 mg, 0.11) were dissolved in H$_2$O (3 mL). To this mixture DIPEA (4.8 µl,) and EDC (21 mg, 0.11) were added. After 2 h 10 mL H$_2$O was added to the mixture and was extracted with DCM. The resulting solution was dried (MgSO$_4$), filtered and evaporated to dryness. Compound 31 was obtained as a white gel in 90% yield (54 mg, 0.025 mmol).

$^1$H NMR (300 MHz, CDCl$_3$) δ; 1.0-2.0 (m, 12H CH$_2$ (Lys)), 3.1 (m, 2H, CH$_2$ (Lys)), 3.4 (s, 6H, OMe (Peg)), 3.3-3.9 (m, 126H, CH$_2$ (Peg), OMe (Lys)), 4.0-4.4 (m, 11H, (2×) CH$_2$—OMe (Peg), (2×) αH (Lys) and CH$_2$ (Gly), CH (Fmoc) and CH$_2$ (Fmoc)), bs (1H, NH), 6.0 (bs, 2H, (2×) NH), 7.1-8.4 (m, 11H, (3×) NH, arom-H (Fmoc))

To a cooled solution (0° C.) of 2.40 g (5.5 mmol) LDI-(HEA)$_2$ in 100 mL CH$_2$Cl$_2$ was added 0.96 g (5.0 mmol, 0.9 equiv.) N-(3-dimethylaminopropyl)-N'-ethylcarbodiimide hydrochloride, 0.68 g (5.0 mmol; 0.9 equiv.) 1-hydroxy-7-azabenzotriazole and 0.87 mL (0.64 g, 5.0 mmol, 0.9 equiv.) N,N-diisopropylethylamine (DiPEA). Subsequently, 4.62 g (5.0 mmol, 0.9 equiv.) Gly-Arg(Pmc)-Gly-Asp(O$^t$Bu)-Ser-(O$^t$Bu)$_2$ was added and the reaction mixture was stirred at ambient temperature. After 18 h the reaction mixture was concentrated under reduced pressure and the residue purified by column chromatography on silica gel using EtOAc/MeOH 95/5 (v/v) as the eluent furnishing pure 33 as a white solid (2.8 g, 42% yield). The product was analyzed by HPLC and $^1$H-NMR.

$^1$H-NMR (300 MHz, DMSO-d6): δ (ppm) 8.26 (1H, t, J=5.1 Hz, NH), 8.21-8.12 (3H, m, 3×NH), 7.97 (1H, d, J=7.8 Hz, NH), 7.92 (1H, d, J=8.0 Hz, NH), 7.49 (1H, d, J=7.8 Hz, NH), 7.24 (1H, t, J=5.5 Hz, NH), 6.92 (1H, bs, NH), 6.52 (1H, bs, NH), 6.37 (2H, m, acryloyl), 6.20 (2H, m, acryloyl), 5.98 (2H, m, acryloyl), 4.73 (1H, q, C$^\alpha$-Asp), 4.33-4.24 (6H, m, 2×O—CH$_2$—CH$_2$—O+C$^\alpha$-Ser+C$^\alpha$-Arg), 4.23-4.16 (4H, m, 2×O—CH$_2$—CH$_2$—O), 3.94 (1H, q, C$^\alpha$-Lys), 3.80-3.71 (6H, m, 2×C$^\alpha$-Gly+C$^\beta$-Ser), 3.05 (2H, q, C$^\epsilon$-Lys), 2.96 (2H, q, C$^\delta$-Arg), 2.70-2.56 (4H, m, CH$_2$CH$_2$ Pmc), 2.49 (s, 6H, 2×CH$_3$ Pmc), 2.06 (3H, s, CH$_3$ Pmc), 1.80 (2H, t, C$^\beta$-Asp), 1.73-1.43 (10H, m, CH$_2$—CH$_2$-Arg, CH$_2$—CH$_2$—CH$_2$-Lys), 1.42 (6H, s, C(CH$_3$)$_2$ Pmc), 1.39 (9H, s, tBu), 1.28 (9H, s, tBu), 1.13 (9H, s, tBu).

Synthesis of LDI-(HEA)$_2$-Gly-Arg-Gly-Asp-Ser (34)

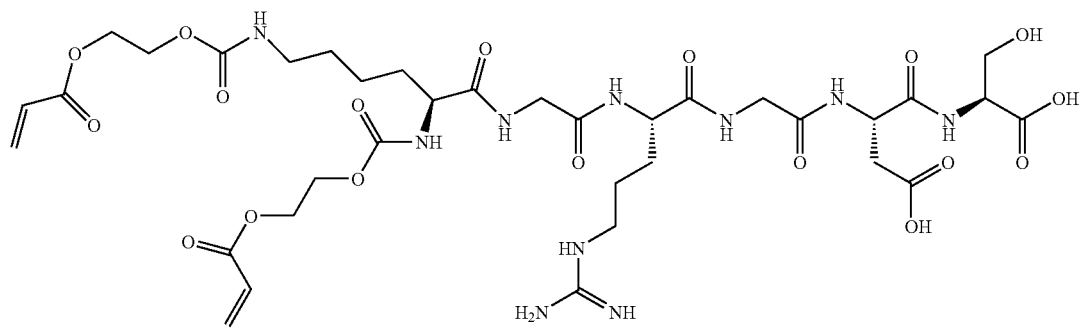

LDI-(HEA)$_2$-Gly-Arg(Pmc)-Gly-Asp(O$^t$Bu)-Ser-(O$^t$Bu)$_2$ (33) (0.76 g, 0.57 mmol) was charged in a sealed Schlenck reactor under a nitrogen atmosphere and at ambient temperature. The reactor was brought under a reduced pressure of 100 mbar. Trifluoroacetic acid (TFA, 5.55 mL) was dosed via a syringe followed by 0.45 mL of 1,3-dimethoxybenzene (to act as scavenger) and the reaction mixture was stirred at ambient temperature. The solution turned from colorless to pink. After 2 h an aliquot was withdrawn from the reaction mixture and analyzed by HPLC showing that the deprotection reaction was not complete. Subsequently, an additional 8.8 mL of TFA was added, the reaction mixture stirred for another 2 h under a reduced pressure of 100 mbar and the TFA removed under reduced pressure. To a solution of the resulting residue in 2.2 mL MeOH was added 200 mL of n-heptane and the resulting white precipitate was isolated by filtration giving pure 34 as a white solid (0.50 g, 0.56 mmol, 99% yield based on 33). The identity of the product was confirmed with $^1$H-NMR and HPLC-MS ([M+H]$^+$=902, as calculated).

HPLC method for monitoring the deprotection reaction: analytical HPLC was performed on an HP1090 Liquid Chromatograph using an Inertsil ODS-3 (150 mm length, 4.6 mm ID) column at 40° C. UV detection was performed at 220 nm using a UVVIS 204 Linear spectrometer. The gradient program was: 0-20 min linear gradient from 5% to 98% buffer B; 20.1-25.0 min 98% buffer B; 25.1-30 min 5% buffer B. Buffer A: 0.5 mL/L methane sulfonic acid (MSA) in H$_2$O; buffer B: 0.5 mL/L MSA in acetonitrile. The flow was 1 mL/min from 0-25.1 min, 2 mL/min from 25.2-29.8 min and 1 mL/min from 29.8-30 min. Injection volumes were 20 μL. HPLC-MS was performed on an Agilent 1100 series system using the same column and identical flow conditions as for analytical HPLC. Retention times: LDI-(HEA)$_2$-Gly-Arg(Pmc)-Gly-Asp(O$^t$Bu)-Ser-(O$^t$Bu)$_2$: 23.98 min; LDI-(HEA)$_2$-Gly-Arg-Gly-Asp-Ser: 9.11 min.

$^1$H-NMR (300 MHz, DMSO-d6): δ (ppm) 12.5 (2H, bs, 2×COOH), 8.30-8.17 (2H, m, 2×NH), 8.13 (1H, t, NH), 8.00-7.91 (2H, m, 2×NH), 7.49-7.38 (2H, m, 2×NH), 7.23 (1H, t, NH), 6.95 (3H, bs, 3×NH), 6.38 (2H, d, acryloyl), 6.19 (2H, m, acryloyl), 5.98 (2H, d, acryloyl), 5.01-4.95 (1H, m, NH), 4.67 (1H, q, C$^α$-Asp), 4.36-4.23 (6H, m, 2×O—CH$_2$—CH$_2$—O+C$^α$-Ser+C$^α$-Arg), 4.23-4.14 (4H, m, 2×O—CH$_2$—CH$_2$—O), 3.92 (1H, q, C$^α$-Lys), 3.82-3.57 (6H, m, 2×C$^α$-Gly+C$^β$-Ser), 3.10 (2H, q, C$^ε$-Lys), 2.94 (2H, q, C$^δ$-Arg), 1.80-1.69 (2H, m, C$^β$-Asp), 1.69-1.44 (10H, m, CH$_2$—CH$_2$-Arg, CH$_2$—CH$_2$—CH$_2$-Lys). HPLC-MS: [M+H]$^+$=902. (as calculated).

Example 2

Photolitographic Patterning of PEG$_{600}$(LDI-HEA)$_2$) with UV Masking Group (32)

Gel 32 was put between two glass cover slips and was covered with water. With a 405 nm laser of a confocal microscope 50 μm squares were irradiated for 20 times with 100% laser intensity. Afterwards the gels were shaken in a flask for 24 h either with MeOH or EtOH to remove nitrosobenzeacetone.

FIG. 1 shows:

Top row: A) Confocal microscopy picture of the gel with cleavable groups B) Irradiation of a 50 μm square in the gel, the cleaved group is fluorescent.

Bottom row A) Blanco gel viewed trough a confocal microscope B) After irradiating a 50 μm square in the gel no fluorescence is observed.

Example 3

Degradation Experiments (Series I)

A clear 75 w % formulation in THF of the oligomers presented in the table below

| Nr. | Sample | Sample (gram) 75 w % | THF (Gram) 25 w % | Irgacure 2959 (mg) 1 w % wrt. Sample |
|---|---|---|---|---|
| 1 | PEG600-(t-Bu-LDI-HEA)$_2$ | 3.233 | 1.08 | 35 |
| 2 | p-(Lac-Cap)1000-(t-Bu-LDI-HEA)$_2$ | 2.713 | 0.90 | 38 |
| 3 | p-(Lac-Gly)1000-diacrylate | 3.771 | 1.26 | 40 |
| 4 | p-(Lac-Gly)1500-triacrylate | 2.155 | 0.72 | 24 |
| 5 | p-(Lac-Gly)1000-(t-Bu-LDI-HEA)$_2$ | 2.622 | 0.87 | 29 |

| Nr. | Sample | Sample (gram) 75 w % | THF (Gram) 25 w % | Irgacure 2959 (mg) 1 w % wrt. Sample |
|---|---|---|---|---|
| 6 | p-(Lac-Gly)1500-(t-Bu-LDI-HEA)$_3$ | 2.099 | 0.70 | 24 |
| 7 | PEG600-diacrylate | 4.021 | 1.34 | 51 |

Coating Preparation

The formulation was applied onto tin float glass plate with the coating doctor blade designed to give 100 μm thick wet coating. This wet film was cured with UV (1 J/cm$^2$) from D-bulb and speed 20 m/s at 22° C. The coatings were dried for 4 hours at 60° C. in the vacuum oven (200 mbar). The resulting cured and dried coating has a film thickness of 50-60 μm. The coatings were used as such.

Sample Preparation for Weight Loss Experiment in RVS Steel Sieves

Figure 2:
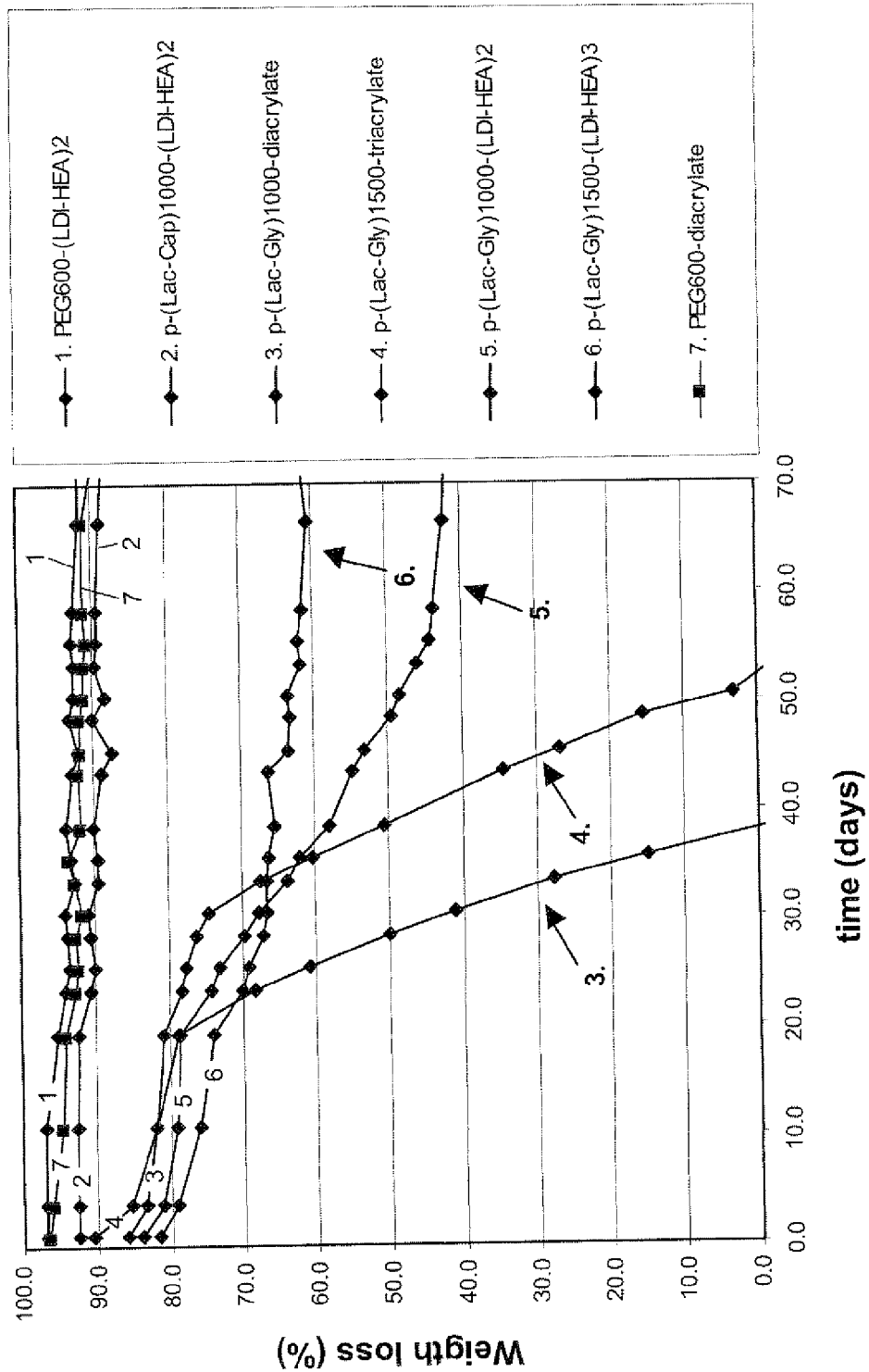
FIGS. 2-4 graphically show the weight loss versus time for the degradation experiment numbers 1-7 (series I) according to Example 3.
Figure 3:
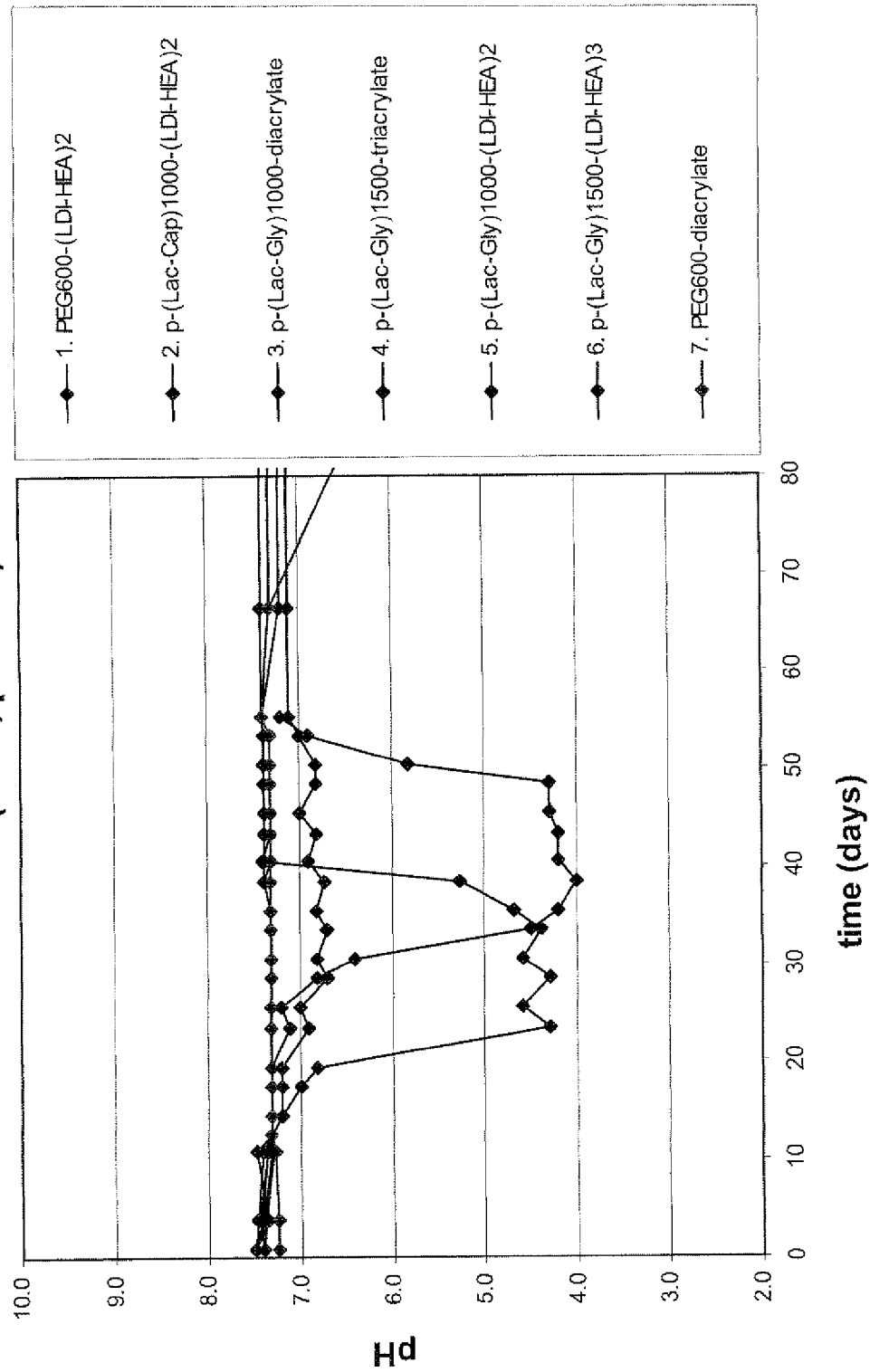
Figure 4:
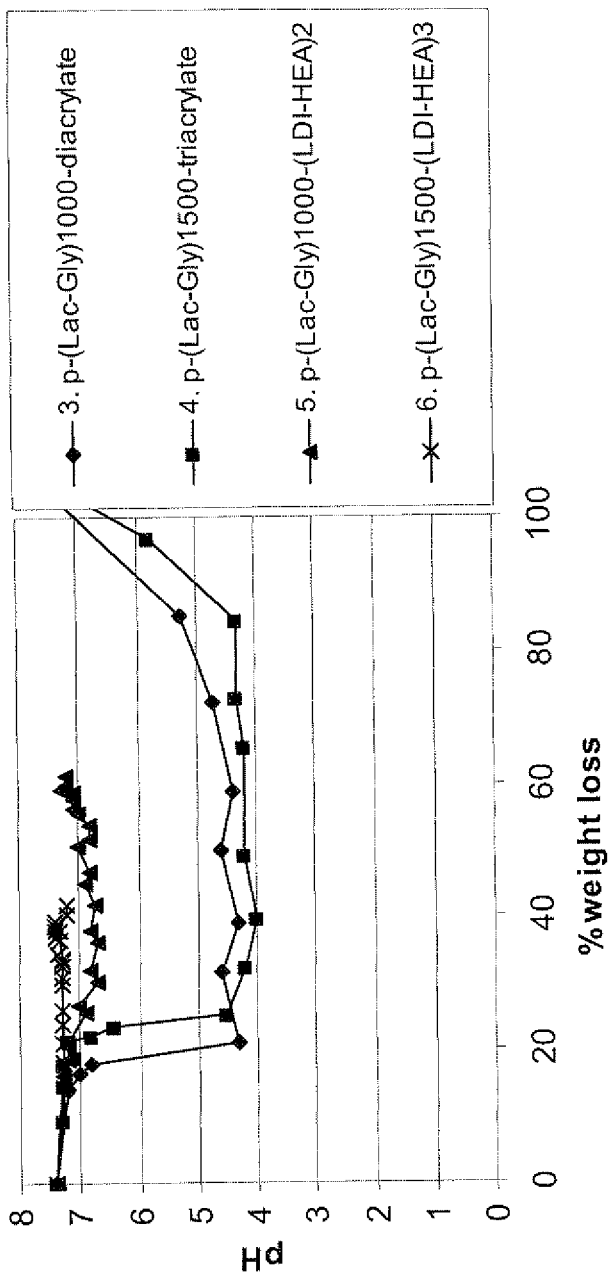
Figure 5:
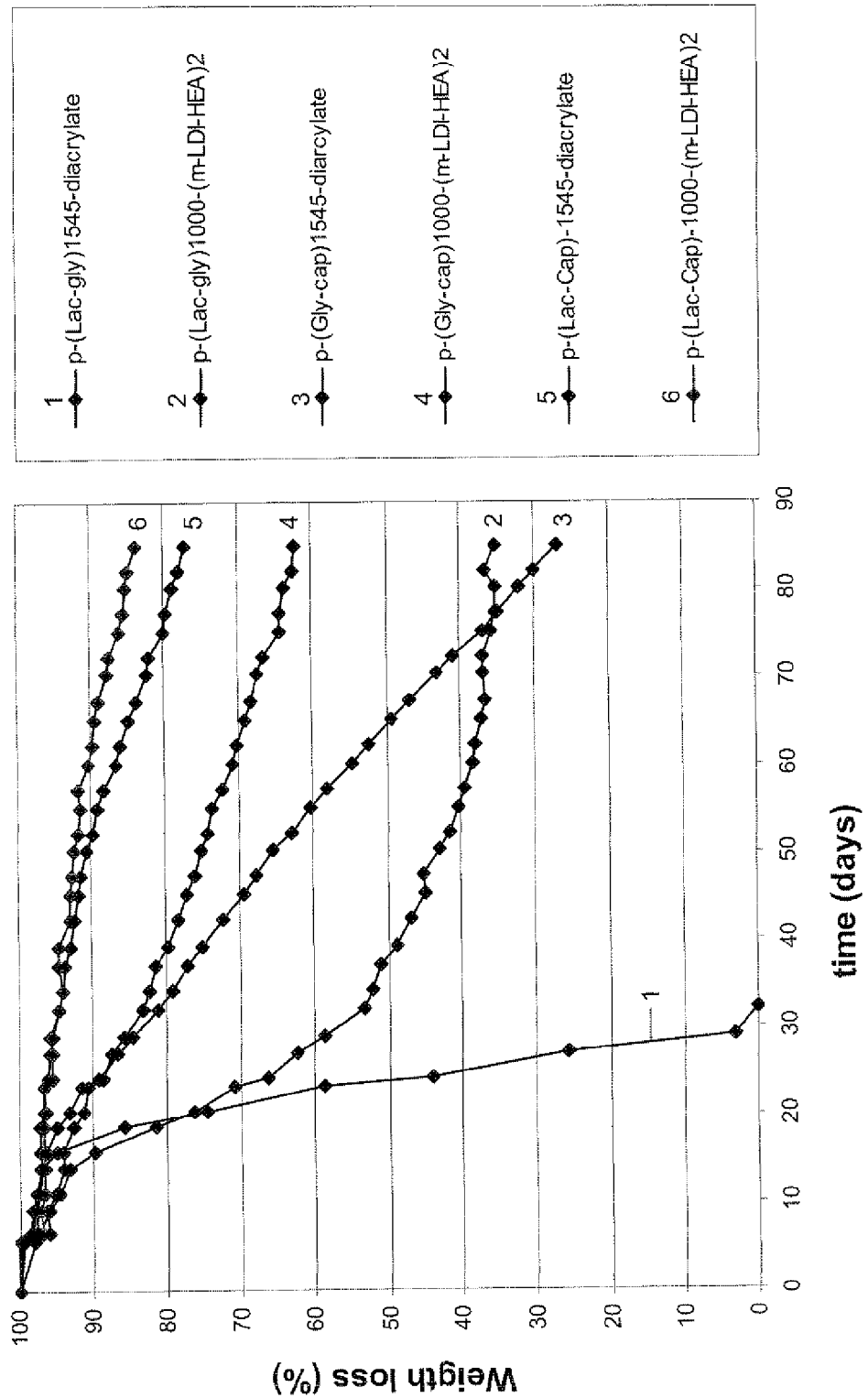
FIGS. 5-10 graphically show the weight loss versus time for the degradation experiment numbers 1-6 (series II) according to Example 4.
Figure 6:
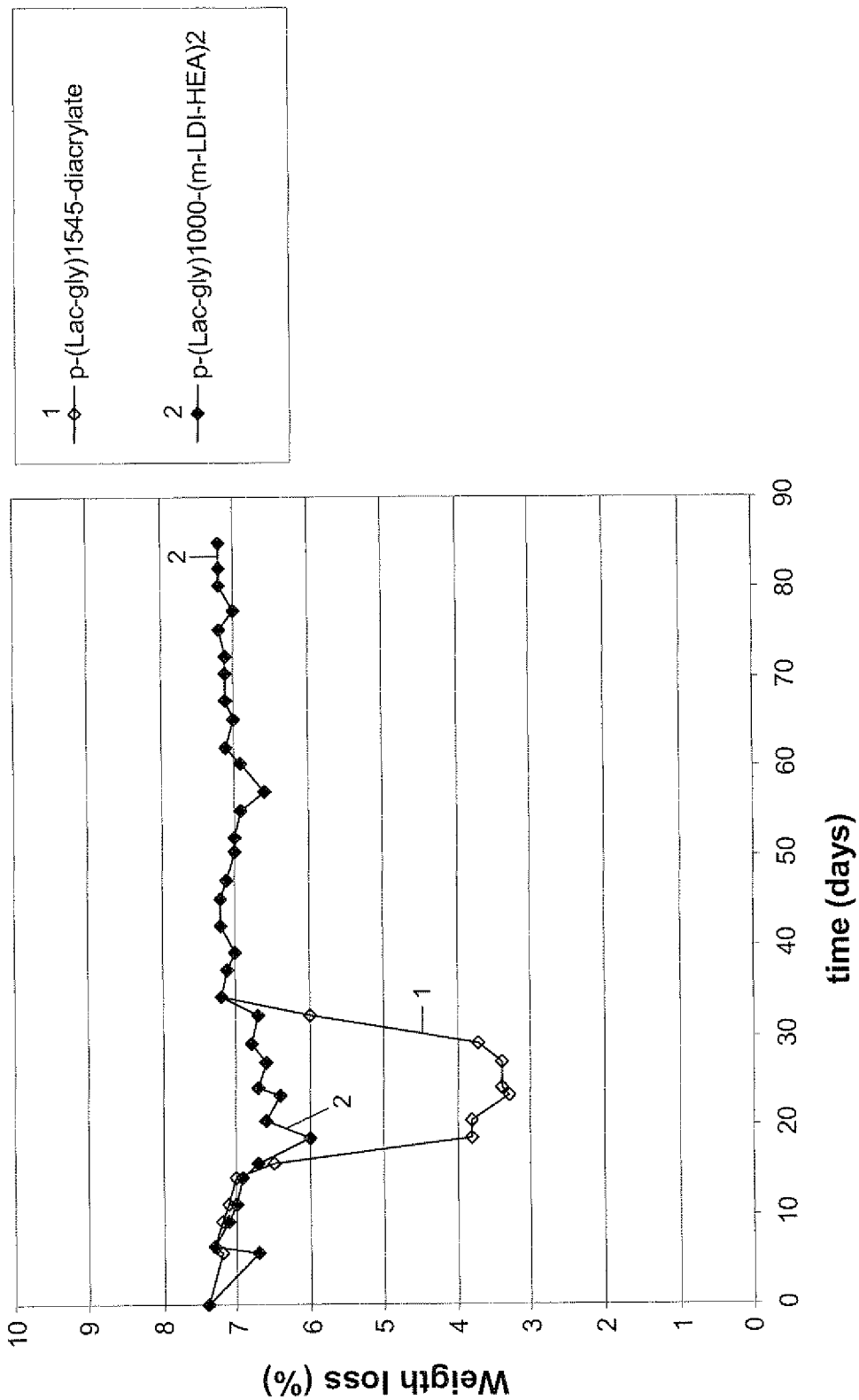
Figure 7:
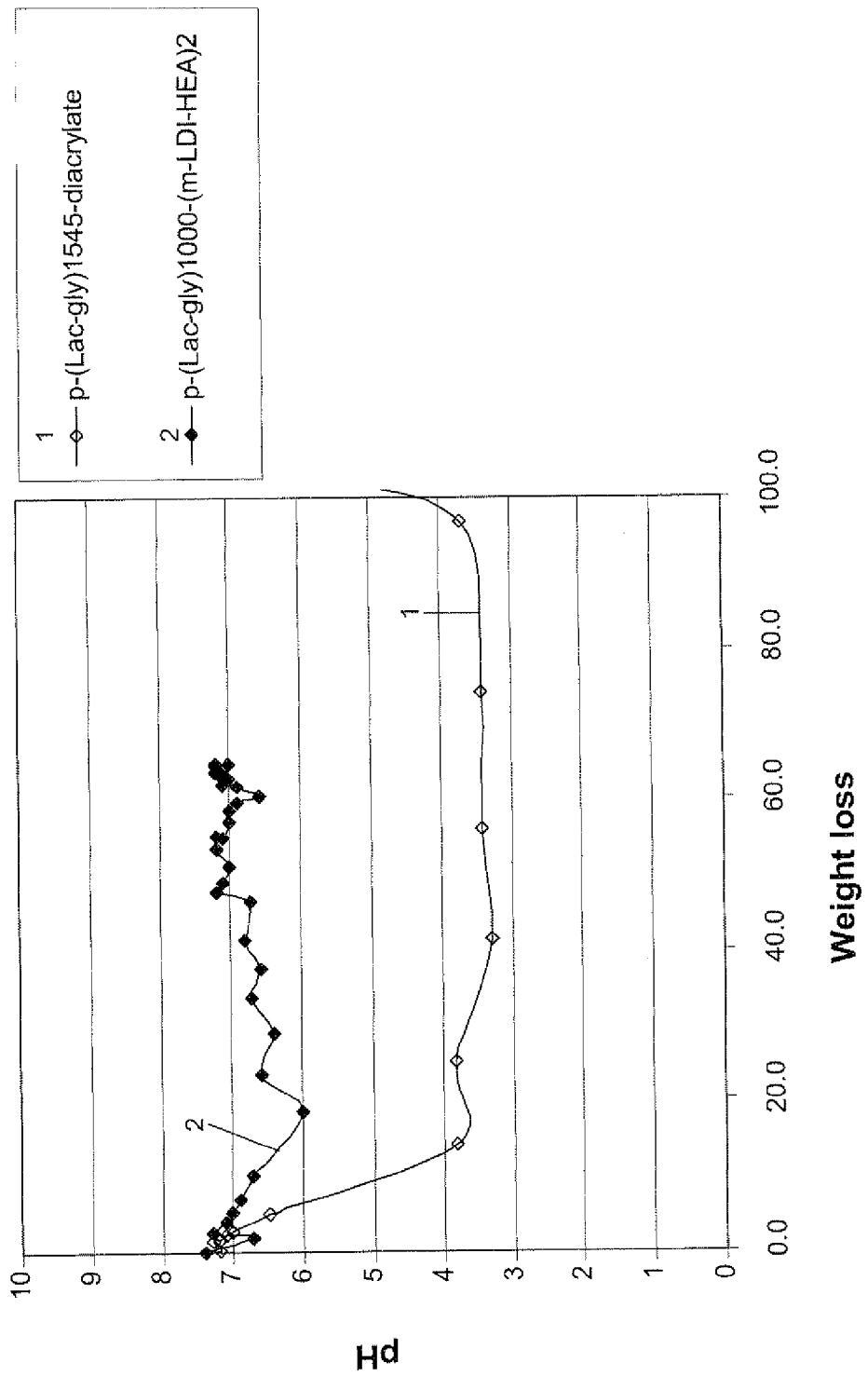
Figure 8:
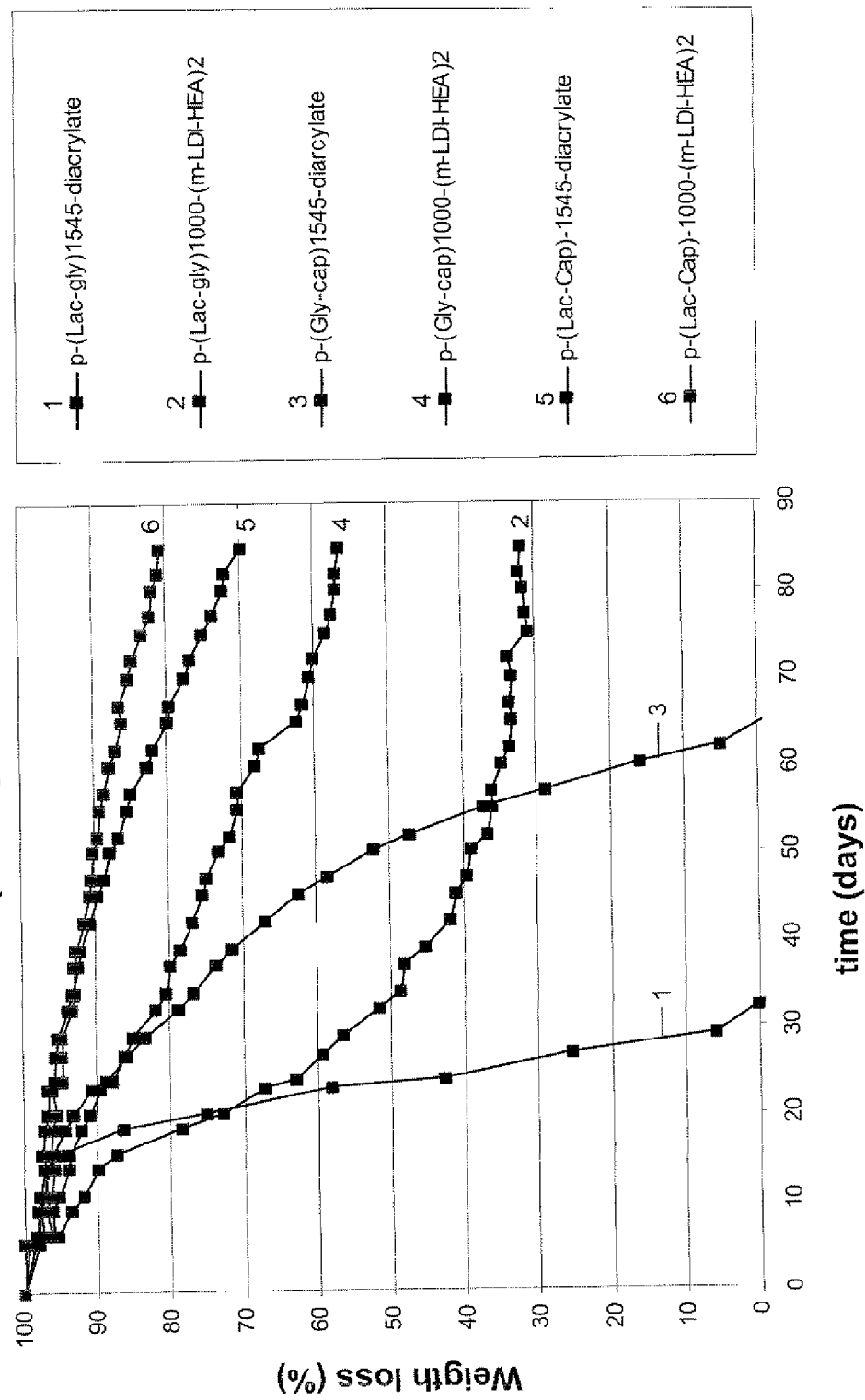
Figure 9:
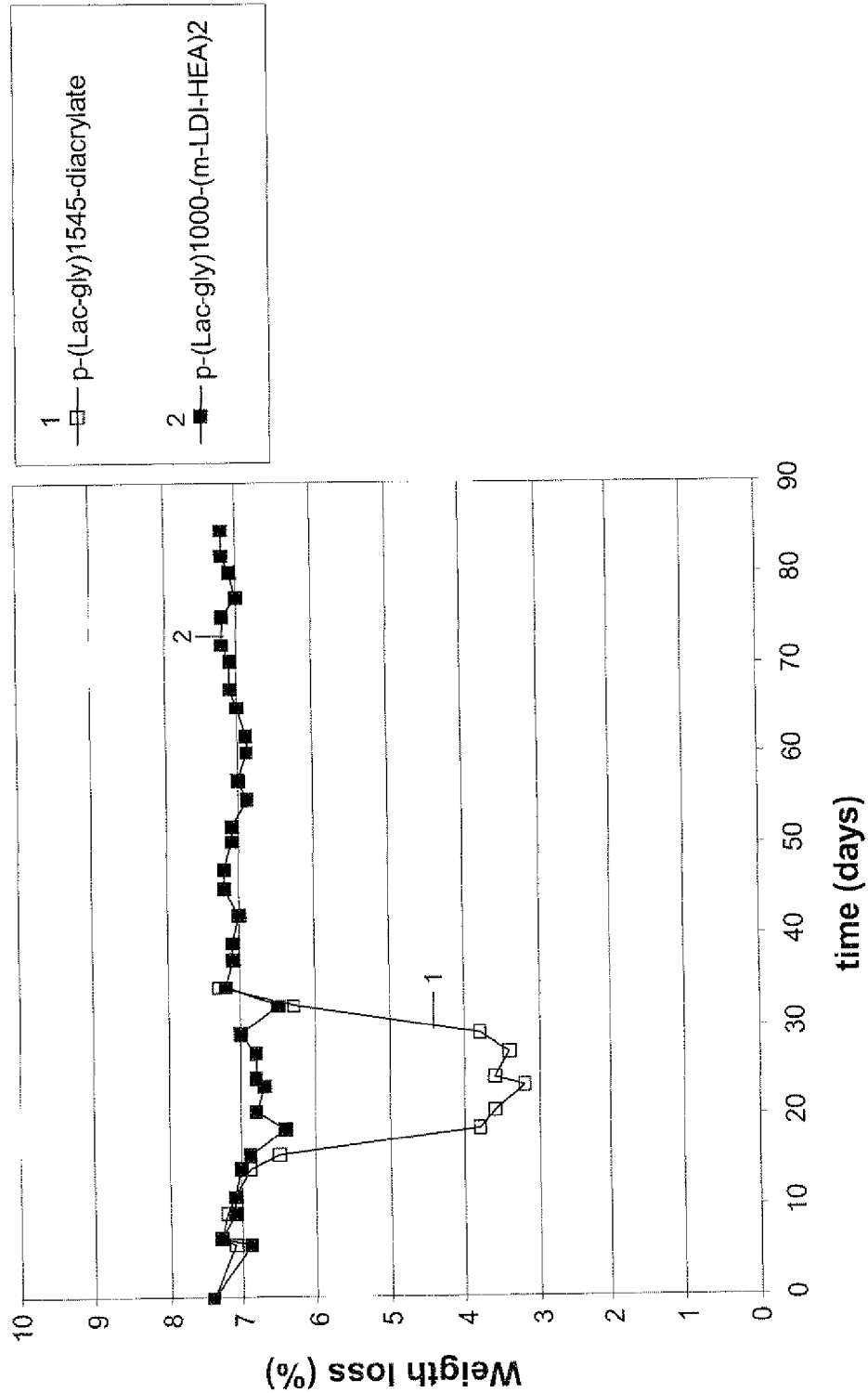
Figure 10:
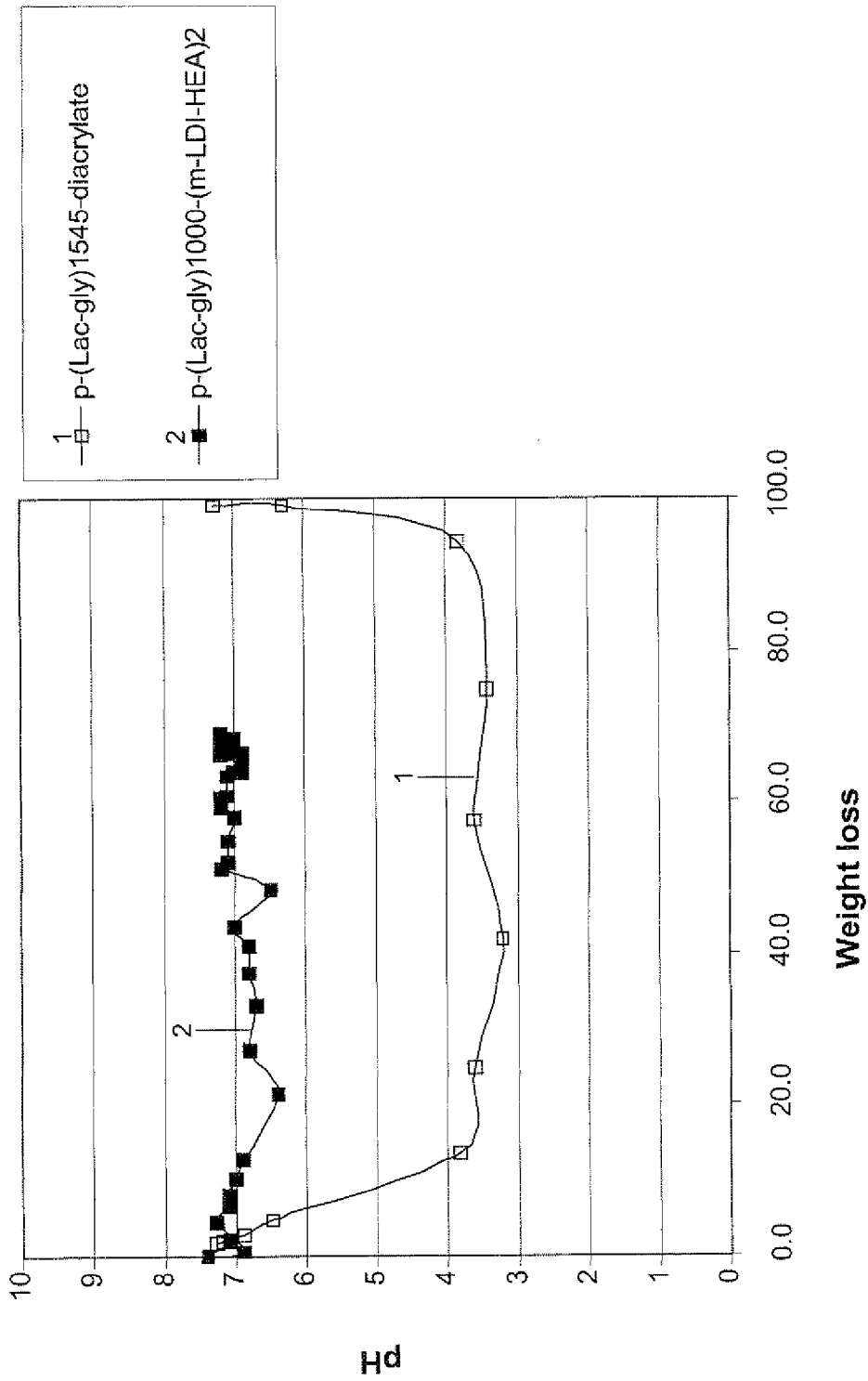

Cured film (~200 mg) was placed in sieves with a mesh size of 350-370 μm. The gel fraction of these coatings was determined via washing with chloroform. Subsequently the coatings were degraded at 37° C. in an aqueous phosphate saline buffer solution (PBS: pH 7.4 via dissolving 0.2 g KCl, 0.2 g KH$_2$PO$_4$, 8 g NaCl and 1.15 g NaHPO$_4$ in 1 liter of water). Every 2-3 days the buffer was changed with fresh buffer. Before adding the fresh buffer the sieves were washed 3 times with 15 mL water, dried overnight at 60° C. and weighed. The degradation was followed by monitoring weight loss, as shown in FIGS. 2-4.

Example 4

Degradation Experiments (Series

A clear 90 w % formulation in THF of the oligomers presented in the table below

| Nr. | Sample | Sample (gram) | THF (Gram) 10 w % | Irgacure 2959 (mg) 1 w % wrt. Acrylates |
|---|---|---|---|---|
| 1 | p-(Lac-gly)1545-diacrylate | 8.89 | 0.99 | 88 |
| 2 | p-(Lac-gly)1000-(m-LDI-HEA)$_2$ | 2.46 | 0.27 | 25 |
| 3 | p-(Gly-cap)1545-diarcylate | 7.98 | 0.89 | 78 |
| 4 | p-(Gly-cap)1000-(m-LDI-HEA)$_2$ | 5.53 | 0.61 | 55 |
| 5 | p-(Lac-Cap)-1545-diacrylate | 8.08 | 0.90 | 78 |
| 6 | p-(Lac-Cap)-1000-(m-LDI-HEA)$_2$ | 5.34 | 0.59 | 53 |

Coating Preparation

The formulation was applied onto tin float glass plate with the coating doctor blade designed to give 200 μm thick wet coating. This wet film was cured with UV (2 J/cm$^2$) from D-bulb and speed 20 m/s at 22° C. The coatings were dried for 4 hours at 60° C. in the vacuum oven (200 mbar). The resulting cured and dried coating has a film thickness of 150 μm. The coatings were used as such.

Sample Preparation for Weight Loss Experiment in RVS Steel Sieves

Cured film (~200 mg) was placed in sieves with a mesh size of 350-370 μm. The gel fraction of these coatings was determined via washing with chloroform. Subsequently the coatings were degraded at 37° C. in an aqueous phosphate saline buffer solution or enzym phosphate buffer solution (PBS: pH 7.4 via dissolving 0.2 g KCl, 0.2 g KH$_2$PO$_4$, 8 g NaCl and 1.15 g NaHPO$_4$ in 1 liter of water, enzym PBS: 28.6 mg of cholesterol esterase was dissolved in 1000 mL PBS buffer).

Every 2-3 days the buffer was changed with fresh buffer. Before adding the fresh buffer the sieves were washed 3 times with 15 mL water, dried overnight at 60° C. and weighed. The degradation was followed by monitoring weight loss, as shown in FIGS. 5-10.

Example 5

Dynamic Mechanical Measurements in Tensile of Coatings.

The materials were delivered as films on a glass plate. The samples for the measurements were punched out of the film. The thickness was measured with the calibrated Heidenhain thickness meter. The dynamic mechanical measurements were done in accordance with ASTM D5026 on equipment of the firm Rheometrics called RSA-III (Rheometrics Solids Analyser III) at a frequency of 1 Hz and over a temperature area of −130° C. tot 250° C. with a heating speed of 5° C./min. During the measurements the storage modulus (E'), the lost modulus (E") and the tangent delta (tan δ) as function of temperature were defined.

Deviation from the ASTM D5026 were:

Allowed temperature deviation ±2° C. (in standard ±1° C.)

Allowed force deviation ±2% (in norm standard ±1%)

Allowed frequency deviation ±2% (in standard ±1%)

Heating speed 5° C./min. (in standard 1 to 2° C./min.)

Test Conditions Tensile Test:

| Tensile test: | |
|---|---|
| Machine: | Zwick 1484. |
| Tensile bar: | Conform DIN 53504 S3a. |
| Force cell: | 10N |
| Strain: | Optical Extensometer (L0 ± 20 mm). |
| Length between clamps: | 35 mm. |
| Test speed: | 50 mm/min |
| Clamps: | 20N clamp |

Mechanical Properties (Series II)

A clear formulation of the oligomers presented in the table below was prepared.

| Sample | Amount (gram) 60 w % | Caprolactone acrylate (SR495) (gram) 40 w % | Irgacure 2959 (mg) (1 w % wrt arcylates) |
|---|---|---|---|
| 1 p-(lactide-caprolactone 50/50)1545-diacrylate | 10.22 | 6.81 | 170 |
| 2 p-(lactide-caprolactone 50/50)1000-(m-LDI-HEA)2 | 9.91 | 6.60 | 165 |

Coating Preparation

The formulation was applied onto tin float glass plate with the coating doctor blade designed to give 200 µm thick coating. This film was cured with UV (1 J/cm$^2$) from D-bulb and speed 20 m/s at 22° C. The resulting cured coating has a film thickness of 180-200 µm. The coatings were used as such.

DMA Results

| nr. | Material | E-mod (37° C.) [MPa] | ε-break [%] | Tg [° C.] |
|---|---|---|---|---|
| 1 | p-(lactide-caprolactone 50/50)1545-diacrylate | 5.55 | 30 | −30 |
| 2 | p-(lactide-caprolactone 50/50)1000-(m-LDI-HEA)$_2$ | 3.99 | 42 | −24 |

Figure 11:
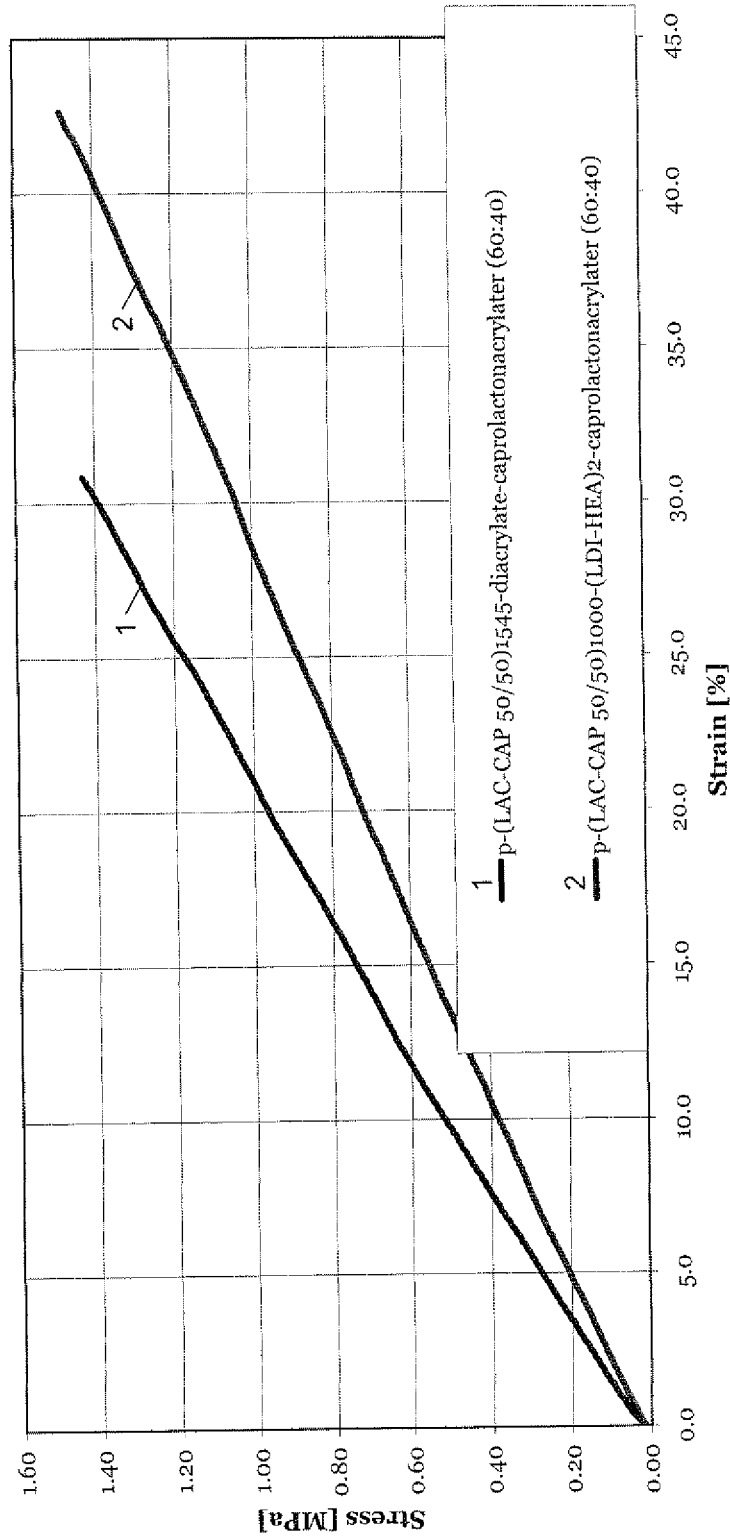
FIG. 11 is a graphical representation of the tensile tests conducted according to Example 5.

FIG. 11 shows a graphical representation of the tensile test.

Example 6

H-Arg(PMC)-OtBu-hexanoate-HEA (18, Monoacrylate, MA) and H-Arg(PMC)-OtBu-hexanoate-LDI-(HEA)$_2$ (19, Diacrylate, DA) were formulated in PTGL1000-(TDI-HEA)$_2$ and PEG600-diacrylate as presented below.

| Nr. | Monoacrylate (mg, mmol) | Diacrylate (mg, mmol) | PTGL1000-(TH)2 (mg) | Irgacure 2959 (mg) 1 w % wrt. Sample |
|---|---|---|---|---|
| 1 | 135, 0.18 | | 1720 | 19 |
| 2 | 68, 0.09 | | 1723 | 18 |
| 3 | | 82, 0.09 | 1714 | 17 |
| 4 | | 82, 0.09 | 1725 | 17 |

| Nr. | Monoacrylate (mg, mmol) | Diacrylate (mg, mmol) | PEG600-diacrylate (mg) | Irgacure 2959 (mg) 1 w % wrt. Sample |
|---|---|---|---|---|
| 5 | 113, 0.15 | | 1527 | 17 |
| 6 | 56, 0.075 | | 1500 | 16 |
| 7 | | 68, 0.075 | 1534 | 17 |
| 8 | | 68, 0.075 | 1818 | 16 |

Coating Preparation

Figure 12:
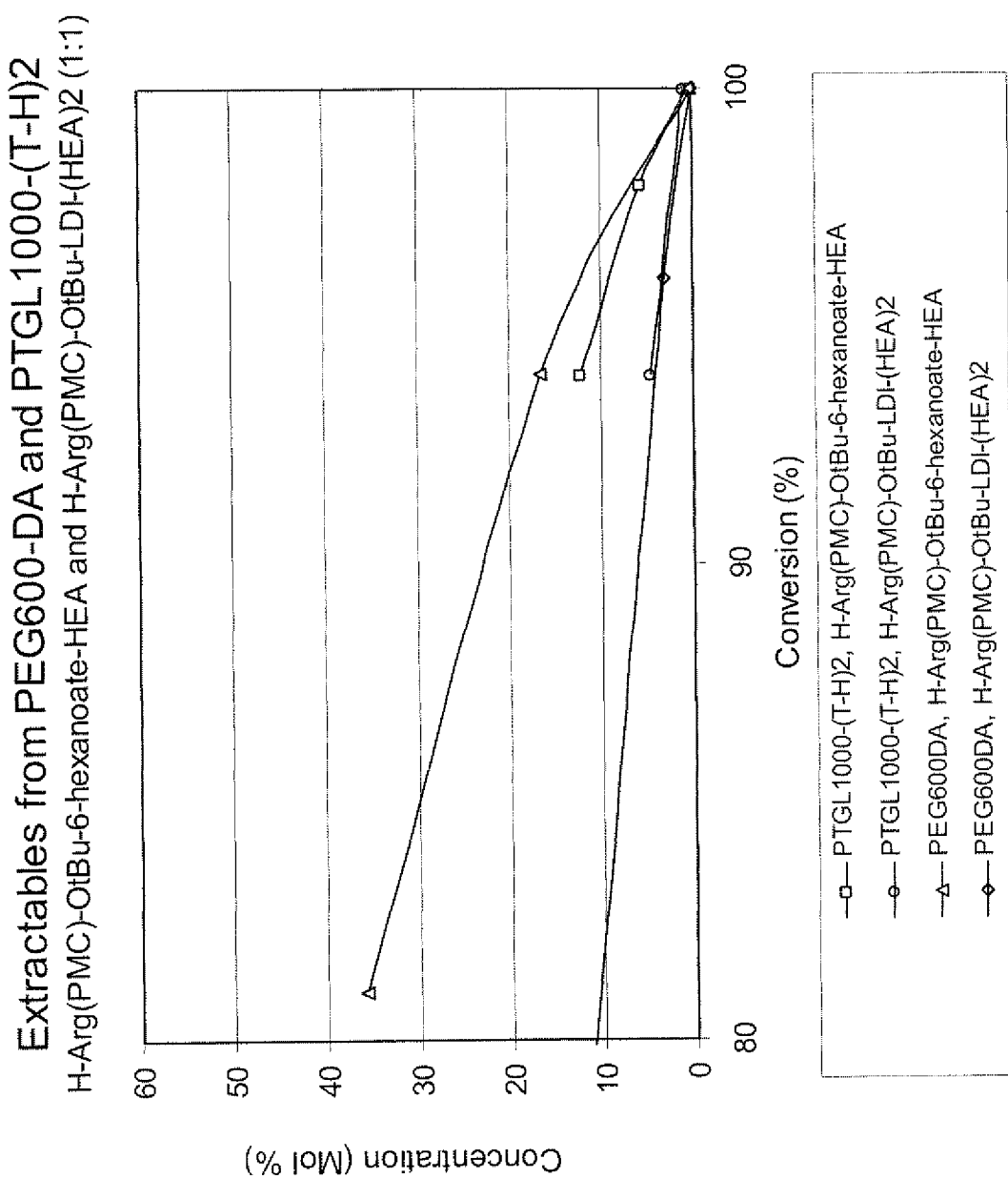
FIGS. 12-13 are graphical representations of the extractable testing conducted according to Example 6.
Figure 13:
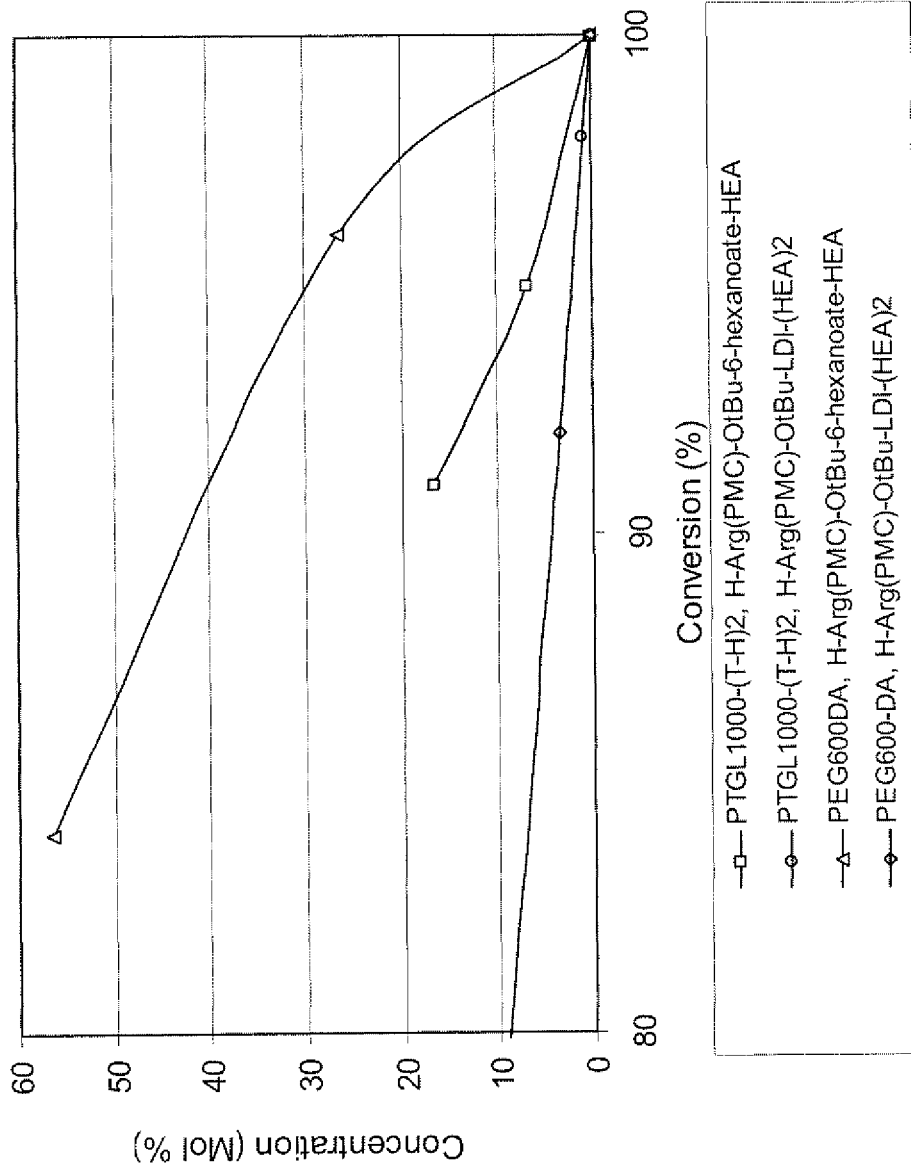

The formulation was applied onto tin float glass plate with the coating doctor blade designed to give 100 µm thick wet coating. This wet film was cured with UV D-bulb and speed 17.5 m/s at 22° C. Different intensities were applied to yield in different acrylate conversion. Formulations 1-4 were cured with the intensities of 0.04 J/cm$^2$, 0.20 J/cm$^2$ and 2.0 J/cm$^2$. Formulations 5-8 were cured with the intensities of 0.09 J/cm$^2$, 0.44 J/cm$^2$ and 2.0 J/cm$^2$. The coatings are used as such. Coatings 1-8 were placed in a vial together with acetonitril. After 1 hour the extractables were measured with HPLC. The results are shown in the FIGS. 12 and 13.

Example 7

A clear 50 w % formulation in MeOH of the oligomers presented in the table below

| Sample | Amount (gram) | RGD-LD1(HEA)2 (17) (gram) | MeOH gram | Irgacure 2959 (mg) (1 w % wrt arcylates) |
|---|---|---|---|---|
| 1 PTGL1000-(TDI-HEA)2 | 6.60 | — | 6.75 | 66 |
| 2 PTGL1000-(TDI-HEA)2 | 6.70 | 0.332 | 7.14 | 67 |

Coatings of PTGL1000-(TDI-HEA)2 control and PTGL1000-(TDI-HEA)2/RGD-LDI-(HEA)2 on glass cover slips could not be used for cell culture experiments, because the coating was not resistant to sterilization conditions (with 70% EtOH). Coating of the polymers on plastic coverslips was much better. The formulation was applied onto Thermanox® PET cover slips (diameter 13 mm) via spin coating (10 sec, 28 rpm). These cover slips were cured with UV (2 J/cm$^2$) from D-bulb and speed 20 m/s at 22° C. The cover slips and coatings were were used as such.

All experiments were carried out using Fibroblasts from human foreskin. Culture 24-well plates were purchased from Corning/Costar. (cat# 3524). The thermanox plastic coverslips were purchased from NUNC (cat# 174950). As control gelatin, 1% (w/v) water, ±200 µl/2 cm2 (Merck, cat#104070) incubated for 1 hour at RT was used. Cyclic RGD: Cyclo(-Arg-Gly-Asp-D-Phe-Val) was purchased from Bachem (cat# H-2574) and dissolved in sterile water (10 mg/). The serum free culture medium contains M199 Cambrex/BioWhittaker, cat# BE12-117F, 100 IU/penicillin, 100 µg/streptomycin (Invitrogen/Gibco, cat# 15140-122).

The plastic cover slips have the tendency to float in the medium in contrast to glass cover slips. Therefore the cover slips had to be "glued" to the bottom of the wells, using paraffin: a droplet (or two) of melted paraffin was applied half on the cover slip and half on the bottom of the well (this was done using a wooden stick). The paraffin was allowed to set for 30 minutes at RT. Then 0.5 mL of 70% (v/v) ethanol was added to the wells and incubated for 30 minutes at RT After this period, the now sterile cover slips were washed 5 times with 1 mL of M199 medium (+pen/strep), (one time they were left for 1 hour at RT). The cover slips with the coatings were now ready to use.

The uncoated cover slips were now incubated with gelatin or vitronectin (1 hour, RT), after which they were washed one more time.

Cells were cultured at 37° C., 5% CO$_2$/95% air, in a humid environment. The cells were seeded (0.5 ml/well) in "high" density, approx. 10000 cells/well Fibroblasts were seeded in complete M199 or M199 containing only pen/strep (serum free medium). (in the latter case cells were washed once with the serum free medium before seeding). To half the cells cyclic RGD was added (50 µg/ml final conc) so the cyclic RGD was present during attachment of the cells. Photographs were taken after: approx. 16 hours (overnight)

To study the effect of c-RGD this peptide was added to the cells (50 µg/mL) before they were seeded (so the cyclic RGD was present during attachment of the cells). Cells were cultured at 37° C., 5% CO2/95% air, in a humid environment.

Figure 14:
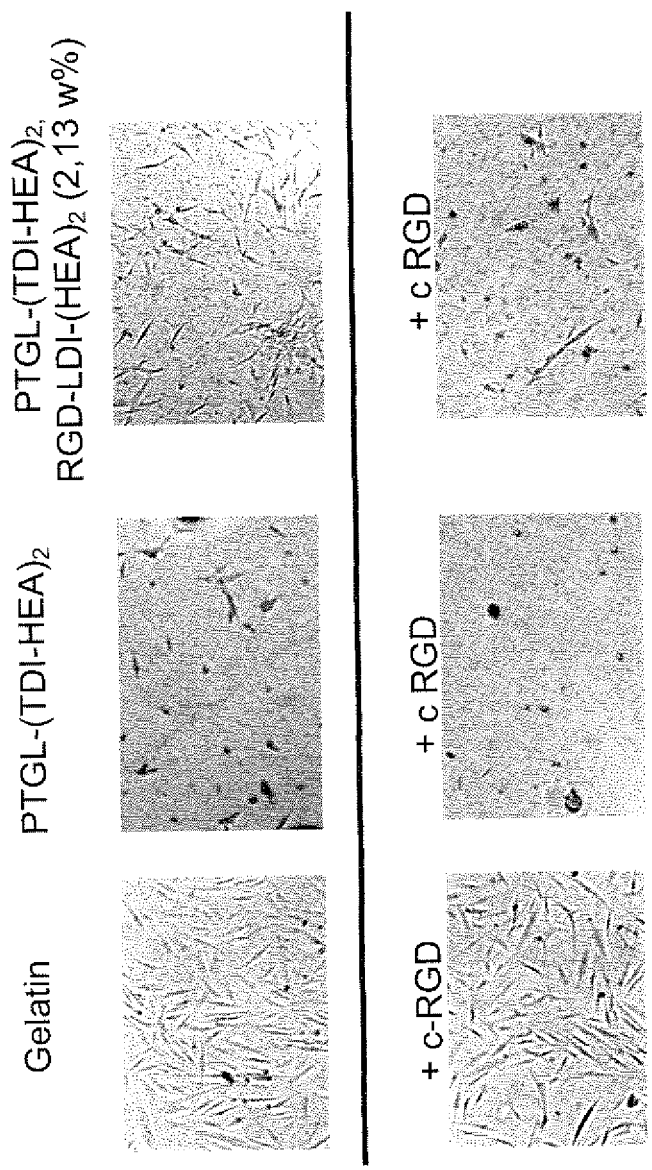
FIGS. 14 and 15 are photographs showing cell attachment properties of PTGL1000-(TDI-HEA)$_2$/RDG-LDI-(HEA)$_2$ and PTGL600-(m-LDI-HEA)$_2$/GRGDS-(LDI-HEA)$_2$ versus control polymers PTGL1000-(TDI-HEA)$_2$ and PEG600-(m-LDI-HEA)$_2$ conducted according to Examples 7 and 8, respectively.

The experiments under serum-free conditions were only carried out using fibroblasts. The PTGL1000-(TDI-HEA)2/RGD-LDI-(HEA)2 coating showed a significant better cell attachment as compared to control polymer, suggesting that the RGD-moiety on the polymer is able to interact with the cells and improve attachment. The morphology of cells grown on PTGL1000-(TDI-HEA)2/RGD-LDI-(HEA)2 coating was better than that of cells grown on PTGL1000-(TDI-HEA)2 coating. FIG. 14 shows photographs, illustrating this.

Example 8

A clear 50 w % formulation of the oligomers in THF are presented in the table below

| Sample | Amount (gram) | GRGDS-LDI(HEA)2 (??) (gram) | THF gram | Daracure 1173 (mg) |
|---|---|---|---|---|
| 1 PEG600-(m-LDI-HEA)$_2$ | 2.75 | — | 6.75 | 40 |
| 2 PEG600-(m-LDI-HEA)$_2$ | 2.50 | 0.200 | 2.70 | 40 |

The formulations of PEG600-(m-LDI-HEA)$_2$ and PEG600-(m-LDI-HEA)$_2$/GRGDS-LDI-(HEMA)$_2$ was applied onto Thermanox® PET cover slips (diameter 13 mm, Thermanox Plastic NUNC, cat# 174950) via spin coating (5 sec, 3000 rpm). These cover slips were cured with UV (5 J/cm$^2$) from D-bulb under nitrogen atmosphere and a speed of 18 m/s at 22° C. The cover slips and coatings were used as such.

All experiments were carried out using Fibroblasts from human foreskin. The 24-well culture plates were purchased form Corning/Costar (cat# 3524). The Thermanox Plastic coverslips were purchased from (NUNC, cat# 174950). As a contol Gelatin, 1% (w/v) water, ±200 µl/2 cm2 (Merck, cat#104070) incubated for 1 hour at RT was used. The Cyclic RGD: Cyclo(-Arg-Gly-Asp-D-Phe-Val) (Bachem, cat# H-2574) was dissolved in sterile water (10 mg/ml) and used as such. The serum free culture medium contains: M199 Cambrex/BioWhittaker, cat# BE12-117F, 100 IU/ml penicillin, 100 µg/ml streptomycin (Invitrogen/Gibco, cat# 15140-122). The serum containing medium contains 199 (Cambrex/BioWhittaker, cat# BE12-117F), 10% human serum, 10% NewBornCalfSerum (NBCS), 150 µg/ml ECGF (Endothelial Cell Growth Factor), 2 mM L-Glutamin, 5 U/ml heparin, 100 IU/ml penicillin and 100 µg/ml streptomycin As fixative_2% formaldehyde+0.2% glutaraldehyde in water was used.

The coverslips were "glued" to the bottom of the wells, using paraffin. The paraffin was melted and 3-4 droplets were applied half on the coverslip and half on the bottom of the well (this was done using a wooden stick). The paraffin was allowed to set for 30 minutes at RT. Then 0.5 ml of 70% (v/v) ethanol was added to the wells and incubated for 30 minutes at RT. After this period, the now sterile coverslips were washed 3 times with 1 ml of M199 medium (+pen/strep), (one time they were left for 1 hour at RT)

During this one hour incubation of the coated coverslips, the uncoated coverslips were incubated with gelatin or vitronectin (1 hour, RT) after which all coverslips were washed one more time. The coverslips were now ready for use.

Cells were cultured at 37° C., 5% CO$_2$/95% air, in a humid environment. The cells were seeded (0.5 ml/well) in "high" density, approx. 30000 cells/well Fibroblasts were seeded in complete M199 or M199 containing only pen/strep (serum free medium). (in the latter case cells were washed once with the serum free medium before seeding). To half the cells cyclic RGD was added (50 µg/ml final conc) so the cyclic RGD was present during attachment of the cells. Photographs were taken after: approx. 16 hours (overnight)

Figure 15:
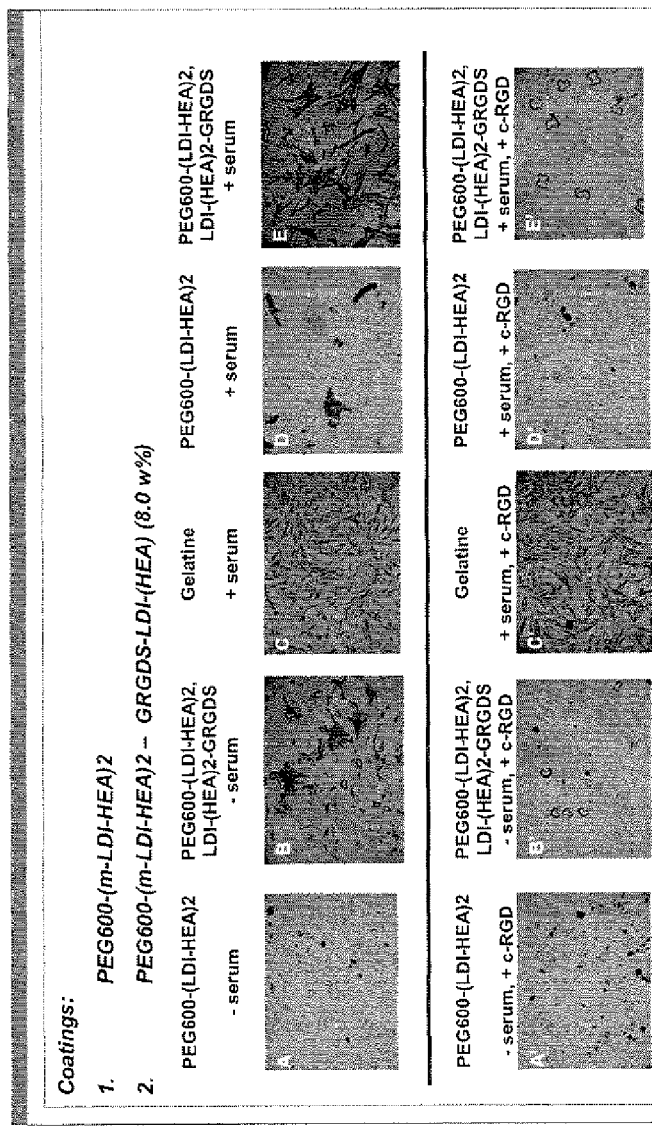

The PEG600-(m-LDI-HEA)$_2$/GRGDS-(LDI-HEA)$_2$ coating showed a significant better cell attachment under serum free and serum containing conditions as compared to control polymer PEG600-(m-LDI-HEA)$_2$, suggesting that the GRGDS-moiety on the polymer is able to interact with the cells and improve attachment. FIG. 15 shows photographs, illustrating this.

The invention claimed is:

1. A compound comprising (a) at least two polymerizable moieties, (b) at least one amino acid residue of an amino acid, the amino acid comprising at least two amine groups, wherein the at least two amine groups of the amino acid have formed a carbamate, a thiocarbamate or a carbamide group, and (c) a biomolecular moiety Z linked directly or via a spacer to a carboxylic acid moiety of the amino acid residue, and wherein the compound is represented by Formula I:

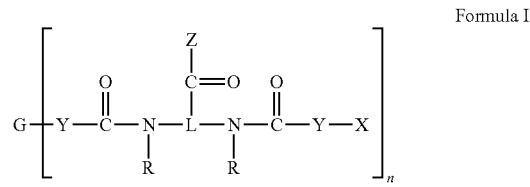

Formula I wherein

G is a residue of a —OH, —NH$_2$, —RNH or SH multifunctional polymer or oligomer selected from the group consisting of polyesters, polythioesters, polyorthoesters, polyamides, polythioethers, polyanhydrides and polydioxanones, wherein R is as defined below, or G is an X as defined below;

each X independently represents a moiety comprising a group that is polymerizable by radical reaction selected from the group consisting of acrylates, alkylacrylates, methacrylates, alkylmethacrylates, vinylethers, fumarates, and vinylsulphones;

each Y independently represents, O, S or NR;

each R independently represents hydrogen or a group selected from substituted and unsubstituted hydrocarbons which optionally contain one or more heteroatoms;

L represents a substituted or unsubstituted hydrocarbon that optionally contains one or more heteroatoms;

n is an integer having a value of 1 if G is an X, and n is at least 2 if G represents a residue of the multifunctional polymer or oligomer; and Z is a biomolecular moiety linked directly or via a spacer to the remainder of the compound.

2. A compound according to claim 1, wherein Z is selected from the group consisting of amino acid residues; peptide residues; carbohydrate residues and nucleotide residues.

3. A compound according to claim 2, wherein Z is selected from a signalling moiety for a cell, a moiety for promoting cell adhesion to the compound, a moiety for controlling cell growth, an antithrombotic moiety, a stimulator for wound healing, a stimulator for the nervous system and an antimicrobial moiety.

4. A compound according to claim 1, wherein L represents a linear or branched C3-C8 alkyl.

5. A compound according to claim 1, wherein the NR-L (C=O)—NR moiety of Formula I represents the residue of a lysine moiety a diaminopropionic acid moiety, a hydroxyllysine moiety, a N-alpha-methylated lysine, or a diaminobutanoic acid moiety.

6. A polymer comprising a reaction product of a formulation comprising the compound according to claim 1.

7. A method for preparing a compound according to claim 1, comprising the step of first reacting a compound of Formula III:

Formula III wherein R is hydrogen or a protecting group,
with a compound of the formula X-Y-H, if G is and X, or if G is not an X, a compound of the formula G-Y-H, wherein the hydrogen or the protecting group of R in Formula III is selectively removed to covalently attach the biomolecular moiety directly or via a spacer to the carboxylic acid moiety attached to L.

8. A method for preparing a polymer comprising the step of polymerizing a compound according to claim 1.

9. An article comprising the polymer according to claim 6.

10. An article comprising a polymer that is a reaction product of a formulation comprising two different compounds according to claim 1 that differ at least by biomolecular moiety Z.

11. An article according to claim 9, wherein the article is selected from the group consisting of microspheres, nanospheres, implants, hydrogels, and artificial body tissues.

12. An article according to claim 9, wherein the article is biocompatible.

13. An article according to claim 9, comprising a surface having at least first and second selected areas each comprised of reaction products of first and second compounds according to claim 1, respectively, wherein the reaction products of the first and second compounds differ from one another at least by bimolecular moiety Z.

14. A method for preparing an article comprising the steps of:

(a) providing an article comprising a polymer, the polymer being a reaction product of a formulation comprising a compound represented by Formula II:

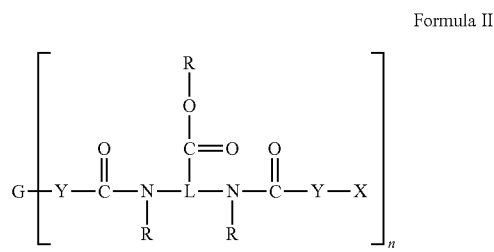

Formula II wherein R is a protecting group or hydrogen;
G is a residue of a —OH, —NH$_2$, —RNH, or —SH multifunctional polymer and oligomer selected from the group consisting of polyesters, polythioesters, polyorthoesters, polyamides, polythioethers, polyanhydrides and polydioxanones, or G is an X as defined below;
each X independently represents a moiety comprising a group that is polymerizable by radical reaction selected from the group consisting of acrylates, alkylacrylates, methacrylates, alkylmethacrylates, vinylethers, fumarates, and vinylsulphones;
each Y independently represents, O, S or NR;
L represents a substituted or unsubstituted hydrocarbon that optionally contains one or more heteroatoms;
n is an integer having a value of 1 if G is an X, and n is at least 2 if G represents a residue of the multifunctional polymer or oligomer; and (b) selectively removing the hydrogen or protecting group at the area at which biomolecular moiety is to be bound; and (c) covalently attaching the biomolecular moiety directly or via a spacer to the carboxylic acid moiety.

15. The method according to claim 14, wherein the protecting group is a photocleavable group, and wherein the step of selectively removing the protecting group is accomplished by selectively irradiating the surface of the polymer with electromagnetic radiation.

16. A formulation comprising the compound according to claim 1 and a photoinitiator.

17. A formulation comprising the compound according to claim 2 and a photoinitiator.

18. A formulation comprising the compound according to claim 1 and a photoinitiator, wherein the biomolecular moiety z is a peptide residue.

19. An article formed by polymerizing the formulation according to claim 17.

20. An article formed by polymerizing the formulation according to claim 18.

* * * * *